United States Patent [19]

Gandolfi et al.

[11] Patent Number: 5,245,039
[45] Date of Patent: Sep. 14, 1993

[54] PROCESS FOR PREPARATION OF ENANTIOMERICALLY PURE POLYSUBSTITUTED 1,4-DIHYDROPYRIDINES

[75] Inventors: Carmelo A. Gandolfi; Marco Frigerio; Carlo Riva; Andrea Zaliani; Giorgio Long; Roberto D. Domenico, all of Milan, Italy

[73] Assignee: Boehringer Mannheim Italia, Milano, Italy

[21] Appl. No.: 743,415

[22] PCT Filed: Feb. 15, 1990

[86] PCT No.: PCT/EP90/00243
§ 371 Date: Aug. 14, 1991
§ 102(e) Date: Aug. 14, 1991

[87] PCT Pub. No.: WO90/09376
PCT Pub. Date: Aug. 23, 1990

[30] Foreign Application Priority Data

Feb. 17, 1989 [IT] Italy ............................ 19477

[51] Int. Cl.$^5$ ............................ C07D 211/86
[52] U.S. Cl. .................... 546/321; 546/323; 546/318; 546/21; 546/286; 546/257; 546/270; 546/283; 546/284; 546/278; 544/333
[58] Field of Search ............... 546/318, 321, 331, 323, 546/21, 286, 257, 270, 283, 284, 278; 544/333

[56] References Cited

FOREIGN PATENT DOCUMENTS

| 0225175 | 6/1987 | European Pat. Off. ............ 546/321 |
| 0273349 | 7/1988 | European Pat. Off. ............ 546/321 |
| 8700836 | 2/1987 | PCT Int'l Appl. ................. 546/321 |

OTHER PUBLICATIONS

Klötzer, Monatsh, Chem. 87, pp. 346–353, 1956.

*Primary Examiner*—Jane T. Fan
*Attorney, Agent, or Firm*—Nikaido, Marmelstein, Murray & Oram

[57] ABSTRACT

A process for the optical resolution of racemic 1,4-dihydropyridines, containing isothioureido groups. Salification of racemic isothioureas with optically active acids produces diasteroisomeric mixtures of isothiouronium salts, that, using conventional techniques, are separated in the individual components to give optically pure isothioureides of 1,4-dihydropyridines and salts thereof with conventional acids. Said optically pure 1,4-dihydropyridines can then be subjected to desulphuration and to different transformations to give to other enantiomerically pure and therapeutically useful 1,4-dihydropyridines.

9 Claims, No Drawings

PROCESS FOR PREPARATION OF ENANTIOMERICALLY PURE POLYSUBSTITUTED 1,4-DIHYDROPYRIDINES

BACKGROUND OF THE INVENTION

A large number of drugs, currently in clinical use, are chiral molecules containing one or more asymmetric centers; in many cases these drugs are used as racemic mixtures even if the therapeutic effect is sometimes due to only one of the isomers forming the racemic mixture.

A great attention is recently directed to the role of stereoselectivity principles in the design of biologically active molecules.

Since the stereoselectivity principle is a general rule in biology rather than an exception, often only one of the components of a racemic mixture (the "eutomer") is the active drug while the other one, that is not complementary to the receptor (the "distomer"), is poorly active, or inactive if not even an antagonist.

Except for a few cases when a racemate is more active, less toxic or of longer (or shorter) duration of action then the single components of the racemic mixture, the use of pure enantiomers instead of racemates is today preferred, in order to reduce the xenobiotic load in the living organism, and to avoid risks of toxic side-effects due to the distomer or tis metabolites (see for example E. J. Ariens, "Stereochemistry, a basis for sophisticated nonsense in pharmacokinetics and clinical pharmacology", Eur. J. Clin. Pharmacol., 26, 663, 1984).

The increasing use of "eutomers" in therapy instead of racemates requires, or course, the development of effective, economic and industrially applicable methods of stereoselective synthesis and/or separation and resolution of diastereoisomers and racemates. Optical resolution is often an expensive process and the majority of the methods involves the loss of 50% of the starting racemic material, at least.

The above considerations apply also to the 1,4-dihydropyridine Ca-antagonist family of drugs, that in the last ten years have been introduced in the market for treatment of several cardiovascular diseases, including hypertension, angina of different aetiologies and different types of arrythmias.

The C-4 carbons atom of 1,4-dihydropyridines (see FIG. 1) is a prochiral atom. When at lest one of the substituents, bound to the $C_2$ and $C_3$ carbon atoms, is different form those on the symmetric $C_6$ and $C_5$ positions of the ring, the C-4 carbon atom is chiral and the compounds are racemates. Nifedipine, (dimethyl, 2,6-dimethyl-4-(2-nitrophenyl) 1,4dihydropyridine-3,5-dicarboxylate) is a symmetrical molecule while many other drugs (for ex. nitrendipine, nimodipine, nisoldipine, nicardipine, niludipine, felodipine, isradipine, ryodipine, Fr 24235, amlodipine and nivaldipine) are chiral 1,4-dihydropyridines that have been used in mammalians and humans as racemates; some of them are already marketed.

Only few dihydropyridines are available for investigation as pure enantiomers, even if it is by now well established that the principles of stereoselectivity apply also to this family of drugs.

Qualitative and quantitative differences between enantiomers of 1,4-dihydropyridines may be shown by "in vitro" studies on tissue preparations or on "in toto" organs (see for example H. Glossmann et al., Arzeneim. Forsch./Drug. Res. 35 (12a), 1917, 1985).

More recently, a report by T. Kazuharu (J. Med. Chem., 29 2504, 1986) point out the importance of stereoselectivity: of the four possible diastereoisomers the S,S enantiomers [(S,S)-YM-09730)] proved to have the greatest potency and the longer duration of action.

The use of enantiomerically pure 1,4-dihydropyridines was recently claims in Ep 0240828 and 0273344.

At present, few and very complex methods are available for preparing enantiomerically pure dihydropyridines.

In absence of basic groups (that could then be salified with optically active acids), the known methods required the selective cleavage of an ester group to form a racemic monocarboxylic acid that is salified with optically pure bases. The mixture of diastereoisomeric salts is separated to recover enantiomerically pure acids that are then esterified with chiral and achiral alcohols to give the desired pure enantiomers. The chiral alcohols used in this esterification process must be pure enantiomers to avoid formation and separation of diasteroisomers. Thus, for instance, the preparation of nicardipine enantiomers (J. Shibanuma et al., Chem. Pharm. Bull., 28, 2809, 1980), involves the synthesis of racemic 1-ethoxy-5-methoxycarbonyl-2,6-dimethyl-4-(3-nitrophenyl)-1,4-dihydropyridine-3-carboxylic acid, crystallization of diastereoisomeric salts with cinchonine and cinchonidine followed by esterification of the obtained S- and R- carboxylic acids with the appropriate amino-alkanol and final elimination of the N-ethoxymethylene protective group. More recently the same procedure and intermediates were used in the synthesis of four YM-09730 diastereoisomers (T. Kazuharu, above cited).

In both cases the synthesis of the racemic acid involves the use of ethoxy-methylene-chloride, whose mutagenicity is well ascertained.

More recently, to overcome this drawback, mono tert-butyl esters have been introduced as precursors of the carboxy group of racemic 1,4-dihydropyridines; tert-butyl esters may be selectively cleaved by reaction with trialkyl silyl iodides (JP Pat. Appln. 1161-263). The procedure is particularly convenient in the absence of other ether and/or thioether groups that could be simultaneously cleaved, when present. Alterative procedures involve the synthesis of diasteroisomeric mixtures of optically active 1,4-dihydropyridines, wherein one of the carboxy groups is esterified by an optically active alcohol. Since the components of the mixture may be separated by fractional crystallization or by chromatographic techniques the subsequent selective removal of the chiral alcohols yield pure enantiomeric acids that are esterified with an achiral alcohol (E. Winger et al. DE 2935451, 1981). Enantiomeric Ca-agonist or Ca-antagonist 4-aryl-5-nitro-1,4-dihydropyridines were prepared using this procedure (EP 186028); the removal of the optically active 2-methoxy-2-phenylethanol was carried out by selective saponification. To achieve total selectivity during the removal of chiral alcohols (made possible by reductive cleavage with zinc in acetic acid), A. J. G. Baxter et al. (Abst. 310, IX Medicinal Chem. Symp., Berlin, 1986) used (S)-1-phenyl-2-trichloroethanol as an alternative for creating diasteroselectivity; in this way both the enantiomers of FPL 61810XX were prepared; only one of them, the (+enantiomer, showed Ca-antagonist properties. The most evident drawbacks of these methods are:

a) expensive and complex operations during the separation of diastereoisomers;
b) availability of unexpensive enantiomerically pure alcohols, that cannot be recycled when removed by reductive cleavage.

Finally, EP 273349 discloses a resolution process comprising the salification with optically active bases of racemic 1,4-(1H)-dihydropyridines carrying a free carboxy group that were presumably obtained by direct Hantzsch synthesis, whose compatibility with the used reagents and esterification methods has to be clarified.

DISCLOSURE OF THE INVENTION

The present invention disclosed a process for the optical resolution of asymmetrical polysubstituted 1,4-dihydropyridines, wherein one of the substituents includes one isothioureido moiety, which process comprising:
a) salification of the isothioureido moiety with chiral acids;
b) separation of the diastereoisomers isothiouronium salts and their transformation into isothioureido moieties or other isothiouronium salts with achiral acids;
c) optional transformation of the compounds obtain in b) by reactions of desulphuration, hydrolysis, S-acylation, S-alkylation, esterification.

For the first time, the present invention discloses a resolution process using isothioureido groups as suitable resolution and salification centers. Two previous known examples of optically active isothiouronium salts involve a resolution process comprising the exchange reaction between salts of optically active carboxylic acids and those of racemic isothiouronium salts with achiral acids and fractional crystallization of the diastereoisomeric mixture (Monatsh. Chem. 87, 346, 1956 and Chemica Scripta 20, 32 1982).

These resolution methods based on an exchange reaction fail to be of general applicability and exhibit many disadvantages, such as:
the use of protic solvent helps the exchange reaction between ionic species but it often makes crystallization of diastereoisomeric salts difficult;
in protic and aqueous solvents, an excess of basic slats may cause the base-catalyzed cleavage of isothiouronium salts so as to release thiols and thiourea or salt thereof;
the co-precipitation of salts (originated from the achiral counter-ions) makes the purification of desired diasteroisomeric isothiouronium salts difficult;
increased costs due to the additional process of salification of the resolving chiral acid with a suitable cation with the risk of decreasing the enantiomeric purity of the resolving acids.

The present invention provides simple and economic methods for the optical resolution comprising the direct reaction of new isothioureas, as free bases, with conventional chiral acids. The advantages of the present process are even more surprising in that, till now, said isothioureas were unknown compounds and thought to be poorly stable and then unsuitable for their use in a resolution process.

Contrary to the known methods, the process of the present invention avoids the use of salts of resolving acid that should be prepared "ad hoc", when not commercially available. The method of the present invention provides also very high yields of enantiomer of high optical purity.

If desired, the overall process may be performed in an one-step procedure without isolating racemic isothioureas, as crystalline intermediates.

Since, in 1,4-dihydropyridines, the isothioureido group may be easily introduced and isothioureas are easily transformed, the process of the invention is particularly flexible and adaptable to different synthetic procedures.

The process and the methods of the present invention may be usefully carried out when an isothioureido group is present in the molecule, independently on its position on the 1,4-dihydropyridine ring. However, according to the disclosure of the present invention, an alkylisothioureido group is preferably linked to the 2- (or 6-) carbon atoms of the 1,4-dihydropyridine ring; said group may be transformed into other groups characterizing many of the known racemic dihydropyridines.

The present invention relates to the preparation of enantiomers of formula I:

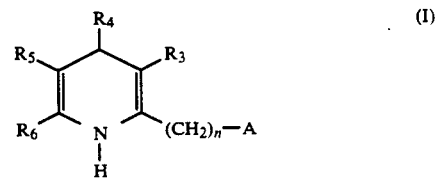

wherein:
A is hydrogen, $-SC-(=N-R_{21})-N-R_{22}-R_{23}$, $-SH$, $-S-(C_1-C_{24})$--acyl, $-SR_2$ or a sulphonium salt of formula $-S(+)R_{26}R_{27}\ Y^{(-)}$;
$R_3$ is a free or esterified carboxy group ($-CO_2R_{31}$);
$R_4$ is a member of selected from the group consisting of:
a substituted or unsubstituted phenyl;
a substituted or unsubstituted $\alpha$- or $\beta$-naphtyl;
a substituted or unsubstituted 5- or 6- membered heterocyclic ring, containing at least one heteroatom selected from N, S and O,
a benzo-fused 5- or 6- membered heterocyclic ring as above defined, preferably linked through the phenyl ring; $R_5$ is a free or esterified carboxy group ($-CO_2R_{32}$), $C\equiv N$, $-NO_2$, $-CO-NH-R_{51}$, $-P(O)(OR_{51})_2$ or a $CO-R_{52}$ group;
$R_6$ is $(C_1-C_6)$-alkyl, $(C_1-C_4)$-halo-alkyl, $-CHO$, $-C\equiv N$, a carboxyester ($-CO_2R_{33}$), an acetal $-CH(OR_{61})(OR_{62})$ or a linear or cyclic thioacetal $-CH(SR_{61})(SR_{62})$:
$R_2$ is a member selected from the group consisting of:
a substituted or unsubstituted phenyl;
a $(CH_2)_n$-Het group wherein Het is an heterocyclic ring as above defined;
a $(C_2-C_6)$alkenyl or alkinyl chain;
a $(C_1-C_6)$alkyl chain unsubstituted or substituted by one or more substituents selected from a free or esterified carboxy group ($-CO_2R_{34}$), $-C\equiv N$, $-O-R_{24}$, $-S-R_{24}$, $-N(R_{24})R_{25}$, Cl, Br, I, a substituted or unsubstituted phenyl, a 5 or 6 membered cycloaliphatic ring optionally substituted by one or more heteroatoms selected from N, S and O; carbonyl, cis or trans oxyrane, and/or aziridine groups;
$R_{21}$, $R_{22}$ and $R_{23}$, are independently selected from hydrogen, $(C_1-C_4)$-alkyl, phenyl-$(C_1-C_4)$-alkyl or $(C_1-C_4)$-acyl, or $R_{21}$ and $R_{22}$ taken together with the carbon atom to which they are linked to form a group $-(CH_2)-_m-$ wherein m is an integer 2 to 4;

$R_{24}$ and $R_{25}$ are independently hydrogen, $(C_1-C_4)$-alkyl, phenyl$(C_1-C_4)$-alkyl, cycano-$(C_1-C_4)$-alkyl, $(C_1-C_4)$-alkoxycarbonyl-$(C_1-C_4)$-alkyl, benzoyl, $(C_1-C_4$-acyl);

$R_{26}$ and $R_{27}$, that can be the same or different, are a $(C_1-C_6)$-alkyl or aryl-$(C_1-C_4)$-alkyl group;

$R_{31}R_{32}$, $R_{33}$ and $R_{34}$, that may be the same or different, are selected from $(C_1-C_4)$-alkyl, $(C_1-C_3)$-alkoxy-$(C_1-C_4)$-alkyl, $(C_2-C_6)$-alkenyl or phenyl-$(C_2-C_6)$-alkenyl, mono-, di- or tri-halo-alkyl;

$R_{51}$ is a $(C_1-C_4)$-alkyl, $(C_1-C_3)$-alkoxy-$(C_1-C_4)$-alkyl, aryl or aryl-$(C_1-C_4)$-alkyl;

$R_{52}$ is a $(C_1-C_4)$-alkyl or phenyl;

$R_{61}$ and $R_{62}$ may be $(C_1-C_4)$-alkyl or phenyl-$(C_1-C_4)$-alkyl, and each of $OR_{61}$, $OR_{62}$, $SR_{61}$ or $SR_{62}$, taken together with the carbon atom to which they are linked, form respectively a 1,3-dioxolane or a 1,3-dithiolane ring, which may be optionally substituted by $(C_1-C_3)$-alkyl or halo-$(C_1-C_3)$-alkyl;

$Y^{(-)}$ is a monovalent anion selected from chlorine, bromine, iodine and $BF_4^{-}(-)$;

$(C_1-C_{24})$acyl is the residue of an aliphatic, aromatic, cycloaliphatic, arylaliphatic, heterocyclic, heteroaliphatic and heteroarylaliphatic carboxylic acid;

n is an integer 1 to 4.

When one of $R_2$, $R_3$, $R_4$, $R_5$ and $R_6$ is a substituted phenyl, the phenyl ring is preferably substituted by one to three substituents, independently selected form halogen (f, Cl, Br, I), nitro, cyano, $-CF_3$, $-CCl_3$, mono- or polyfluoroalkyl (1 to 5 C-atoms), formyl, $(C_1-C_4)$-alkyl, $(C_1-C_4)$-alkoxy, phenoxy, $OCH_2F$, $OCF_3$, mono- or polyfluoroalkylthio (1to 5 C-atoms), alkylsulphinyl (1 to 5 C-atoms), $-CONH_2$, $-SO_2NH_2$, $-SO_2NH$-$(C_1-C_4)$-alkyl, azido, $(C_1-C_4)$-alkylthio, $(C_1-C_4)$-acylamino, $NH-CO_2-$ $(C_1-C_4)$-alkyl, $-NH$-$SO_2C_6H_5$, mono-$(C_1-C_4)$-alkylamino, di-$(C_1-C_4)$-alkylamino, $-CO_2R_{31}$, cis- or trans-$(C_2-C_6$-alkenyl-$CO_2R_{31}$, cis- or trans -$(C_2-C_6)$-alkynyl-C$\equiv$N, $(C_2-C_6)$-lkynyl -$CO_2R_{31}$, $(C_2-C_6)$-alkynyl-C$\equiv$N.

The substituted 5- or 6-membered heterocyclic ring of $R_2$ and $R_4$ may be substituted by one to three substituents independently selected from the group consisting of phenyl-$(C_1-C_4)$-alkyl, $(C_2-C_4)$-alkenyl, $(C_2-C_4)$-alkynyl, $(C_1-C_4)$-alkylthio, $(C_1-C_4)$-alkoxy, $-COR_{31}$, C$\equiv$N, $-CONH_2$, amino, mono-$(C_1-C_4)$-alkylamino, di-$(C_1-C_5)$-alkylamino, Cl, Br, F, mono- or polyfluoro $(C_1-C_5)$-alkyl, nitro, azido, $(C_1C_4)$-acylamino, $(C_1-C_4)$-alkyl sulfonylamino, phenyl, p-tolysulfonylamino, $-SO_2NH_2$, $SO_2-(C_1-C_4)$-alkyl, C$=$O, C$=$S or N O.

Examples of the compounds of formula I and of the appropriate meanings of he various substituents in said compounds are disclosed, for instance, in WO-/EP/8700836.

The enantiomers of formula I are prepared by a process comprising:

a) salification of an enantiomer of a chiral acid of formula HB* with a racemic isothiourea of formula II

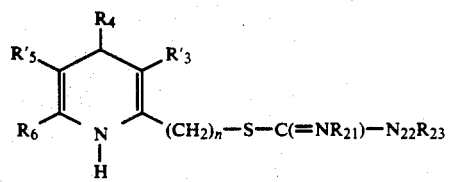

where $R_{21}$, $R_{22}$, $R_{23}$, $R_4$, $R_6$ and n are as above defined, $R_3'$ And $R_5'$ are the same as the above specified $R_3$ and $R_5$, with the proviso that a free carboxy group is excluded;

b) separation of the diastereoisomeric salt of formula (Ia$_1$.HB*) from that of formula (Ia$_2$.HB*) and optional transformation of each salt into the respective free base, i.e. the isothiourea of formula Ia$_1$ or Ia$_2$

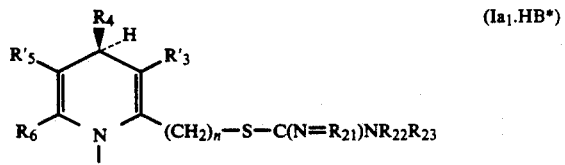

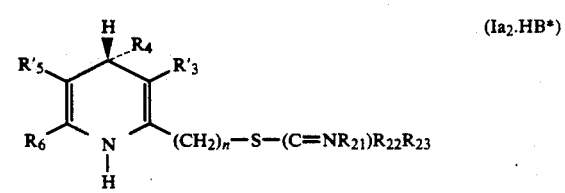

wherein $R_3'$, $R_4$, $R_5'$, $R_6$, $R_{21}$, $R_{22}$, $R_{23}$ and n are as above defined, and, if desired, said free base is then transformed into other isothiouronium salts by treatment with achiral acids;

c) optional transformation of an enantiomeric isothiourea of formula Ia$_1$, Ia$_2$ (or of a salt thereof) into another enantiomer of formula I$_1$ and I$_2$ respectively wherein A' is SH, S$-$$(C_1-C_{24})$acyl, $-SR_2$, or $-S^{(+)}(R_{26})R_{27}Y^{(-)}$; being $R_2$, $R_3$, $R_4$, $R_5$, $R_6$, $R_{26}$, $R_{27}$, $Y^{(-)}$ and n as above defined;

d) optional desulfuration of an enantiomer of formula I$_1$, I$_2$, Ia$_1$ or Ia$_2$ to obtain an enantiomer of formula I wherein A is hydrogen.

A further peculiar embodiment of the present invention is a method for preparing a pure enantiomer of formula I form a racemic compound of formula I' wherein $R_3$ and $R_5$ are carboxyester groups different from each other so as to make possible their selective, independent cleavage, and $-(CH_2)_n-A$ and $R_6$ are the same groups or one of them can be transformed into the other one.

Step by step, selective and differentiated cleavage of one of the two $R_3$ and $R_5$ ester groups yields a mono carboxylic acid that can then be esterified again (or optionally transformed into an amide $-CO-N$-$H-R_{51}$) according to different sequences so that an enantiomer may be transformed into the opposite one.

The following reaction scheme illustrates said aspect of the invention, making reference to enantiomers of formula I' wherein both $(CH_2)_nA$ and $R_6$ are methyl. N and M are ester residues which can be selectively and independently cleaved: allyl esters are particularly preferred groups either for $-CO_2N$ or $-CO_2M$.

The same reaction scheme is also applicable when $(CH_2)_nA$ and $R_6$ are different, provided that one of them is transformed into the other one somewhere in the synthetic route.

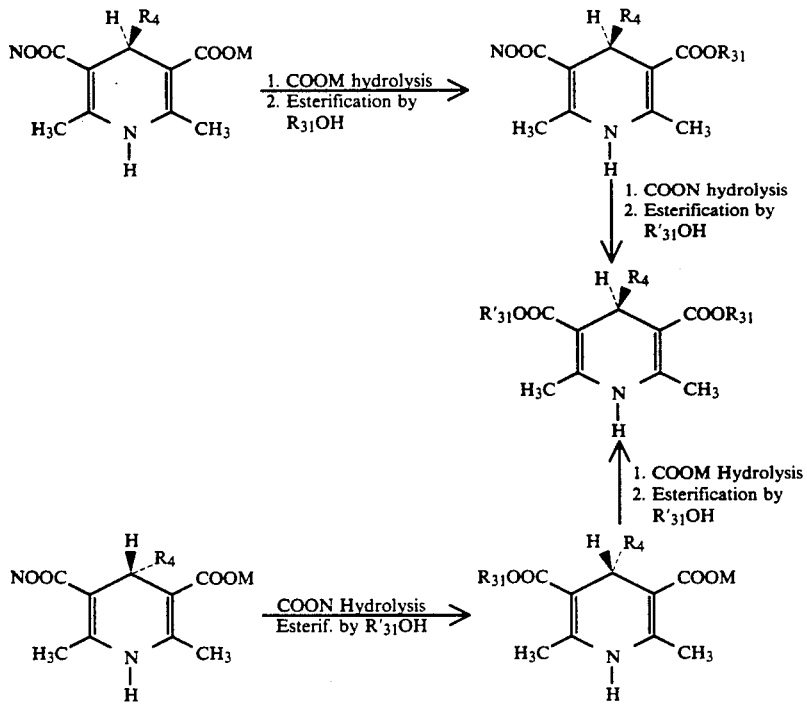

Diasteroisomeric mixtures of salts and/or amides can be obtained by treatment of a racemic isothiourea of formula II with chiral enantiomeric acids. These mixtures are then subjected to optical resolution processes based, for instance, on separation of diastereoisomers by crystallization, distillation, filtration, extraction, thin layer chromatography and/or by high, low or room pressure chromatography on inert or chiral supports, using known procedures, including the crystallization of diastereoisomeric mixtures from enantiomerically pure chiral solvents.

The preferred resolution technique of a racemate of formula II comprises the salification of said racemate with an enantiomerically pure chiral acid HB* to form a diastereoisomeric mixture of isothiouronium salts of formula (II.HB*) that is then separated into the single, diastereoisomerically pure, salts of formulae (Ia$_1$.HB*) and (Ia$_2$.HB*), respectively.

This separation is preferably carried out by fractional crystallization, in solvents such as: water, ($C_1$–$C_5$)-alcohol, ($C_1$–$C_3$)-alkyl acetates and/or formates (ethyl acetate), cycloaliphatic or aromatic hydrocarbons, (Cyclohexane, benzene, toluene, o-, m-, p-xylene;) ethers (tetrahydrofuran, dimethoxyethane, 1,4-dioxane, methylale, diethylether); ketones, (acetone and methylethylketone); amides (formamide, N,N-dimethylformamide, N-methylpyrrolidone), sulphoxides (dimethylsulphoxide) and the like or mixtures thereof.

In general, the preferred enantiomerically pure chiral acids HB* are those allowing the best possible resolution process with the minimum number of recrystallizations.

In the specific case of the present invention, a complete or almost complete separation of the diastereoisomeric pure salts of formula (Ia$_1$.HB*) from those of formula (Ia$_2$.HB*) is often obtained at the first crystallization step; one or at most two recrystallizations are enough to reach optical purities of 99.9% or more. Cheap and conventional optically pure acids, widely available, are very effective and may be conveniently used.

Suitable examples of said acids are: camphoric, mandelic, abietic, 3-bromo-campho-10-sulphonic acids; tartaric acid and its 0,0'-diesters, such as 0,0'-dibenzoyltartaric or 0,0'-di-p-tolyltartaric; malic acids and the esters thereof, α-methoxy-phenylacetic acid, α-methoxy-α-trifluoromethyl-phenylacetic acid; α-aminoacids and amides thereof, such as alanine, proline, phenylglycine, phenylalanine, threonine, cysteine, cystine, homocysteine, homocystine, aspartic and glutamic acids and amides such as: N-benzoyl, N-acetyl, N-phtaloyl, N-BOC or N-tert-butoxycarbonyl amides; or 1,3-thiazolidine-4-carboxylic or N-thia-3-aza-cyclo-hexane-4-carboxylic acids and amides thereof (e.g. N-benzoyl, N-acetyl, N-BOC); chiral phophonic acids, etc. The present invention includes also the resolution agents that have not been specifically mentioned herein. The salification process of a racemate of formula II with an enantiomerically pure chiral acid HB* is carried out in a solute/solvent ratio ranging from 5 ml to 60 ml of solvent for 1 g of salt, at temperatures ranging from about room temperature to the reflux temperature of the solvent, to obtain complete dissolution of the reagents. Hot solutions are left to cool to temperature compatible with the freezing point of the solvent in the range from −30° C. to +50° C., to crystallize the less soluble diastereoisomeric salt of formula (Ia$_1$HB*), that is then separated by filtration and/or centrifugation. Preferably the reaction is carried out at room temperature, using a solvent alone rather than a mixture of solvents.

Since thioureas, like racemates of formula (II) or the single enantiomers of formula (Ia$_1$) and/or (Ia$_2$), are monobasic species, polybasic resolving acids HB* may be used in the range from equimolecular to equivalent amounts; equimolecular amounts are preferred.

During the resolution process, the mother liquors from the crystallization of the less soluble diastereoisomeric salt are enriched in the other enantiomer that, if desired, may be recovered as isothiourea free base, by treatment of said mother liquors with stoichiometrical or slightly higher amounts of bases. Said bases can be selected from an hydrate, bicarbonate or carbonate of an alkali or alkali-earth metal in solid form or a diluted aqueous solutions. As an alternative, neutralization is carried out by treatment with ammonia or its aqueous solutions. The crude enriched isothioureido enantiomer, as free base, may be subjected to resolution by salification with the opposite optical antipode of the previous HB* resolving acid. In this connection, during the neutralization process, particularly preferred solvents are those (for example ethyl acetate, benzene and toluene), that are immiscible with water and are suitable to maintain the isothioureas dissolved as free bases in the organic phase. At the same time, the chiral resolving acids are removed in the aqueous phase with aqueous alkaline washings that are collected and acidified to recover the chiral acids that may then be recycled. Enantiomerically pure isothiouronium salts of formulae (Ia$_1$.HB*) and (Ia$_2$.HB*) are obtained in yields ranging from 7--75% to a value even higher than 85-90%. After recovery of an isothiourea of formula Ia from its isothiouronium salt (Ia.HB*), as above described, the enantiomeric acid HB* is also recovered in high yields, 85-90% at least.

Transformation of an isothiouronium salt of formula (II.HB) or (Ia$_1$.HB*) and/or (Ia$_2$.HB*) into its isothiourea, as free base, of formula IIa, Ia$_1$ or Ia$_2$ is preferably carried out under inert gas atmosphere, at temperatures ranging from 9° C. to 40° C., and preferably from 5° C. to 20° C. If desired, enantiomeric isothioureas of formula Ia$_1$ or Ia$_2$ may be salified with achiral acids to give isothiouronium salts of formula (Ia$_1$.HB) and/or (Ia$_2$.HB).

A suspensions of an appropriate isothiouronium salt of formulae (II.HB, Ia$_1$.HB, Ia$_1$.HB*, Ia$_2$.HB or Ia$_2$.HB*) in a suitable solvent such as (C$_1$-C$_5$)-alcohols, an aromatic hydrocarbon (Benzen, toluene), a halogenated hydrocarbon (dichloromethane or 1,2-dichloroethane), an ester as a (C$_1$-C$_3$)-alkyl formate and/or acetate), water or mixtures thereof can be transformed into an isothiourea of formulae (II, Ia$_1$ or Ia$_2$) by treatment with concentrated aqueous solutions of an inorganic base, for example alkali or alkali-earth hydroxides, bicarbonates and/or carbonate, ammonia and its aqueous solutions, or with solutions of (C$_1$-C$_3$)-dialkyl- or (C$_1$-C$_3$)-trialkylamine in said solvents. The reaction si preferably carried out by treating vigorously stirred suspension of said isothiouronium salts in lower alcohols, for example methanol or ethanol, with aqueous solutions containing at least equimolar amounts of a base such as sodium or potassium hydroxide, bicarbonate or carbonate at 5°-20° C., for a time ranging from few minutes to 12 hours.

It is particularly preferred the gradual addition of equimolar amounts of a base to a vigorously stirred suspension of isothiouronium salt in a mixture of water and a water-immiscible solvent to secure dissolution in the organic phase of the isothiourea that is formed by ion exchange reaction. If desired, at the end of the ion exchange reaction the organic phase may be separated and washed to neutrality, dried and then the isothiourea as free base may be isolate din crystalline form by concentrating the solution under vacuum.

In the specific case of the compounds of the present invention, the above reaction conditions are particularly mild and suitable for preparing isothioureas of high purity, in almost quantitative yields, from isothiouronium salts, even though the latter are known to be easily cleaved and converted into mercaptanes by treatment with dilute aqueous weak bases. In facet, a known method for the preparation of thiols involves the reaction of alkyl halides (or sulphonic esters) with thiourea or N-alkyl isothiourea to give isothiouronium salts, that are hydrolyzed to thiols by treatment with aqueous bases. In opposition to thiols that are easily oxydized to disulphides, the isothiouronium salts are quite stable to air oxydation and since they can be easily converted, they are preferred in organic synthesis and used as masked thiol groups.

Accordingly, when desired, mercaptanes of formula (I) wherein A is SH may be prepared form pure enantiomeric isothiouronium slats of formula (Ia$_1$.HB, Ia$_1$.HB*, Ia$_2$.HB and/or Ia$_2$.HB*) by treatment with diluted aqueous bases: said thiols may then be transformed into another compound of formula (I) wherein A is —S—(C$_1$-C$_{24}$)-acyl by reaction with a suitable activated form (such as anhydride, mixed anhydride, imidazolide, chloride) of a C$_1$-C$_{24}$-aliphatic, cycloaliphatic, aromatic, arylaliphatic or heteroaromatic acid, etc.

Racemic isothiouronium salts of formula II wherein n is the integer 1 and B is preferably chlorine or the residue of a monovalent achiral organic acid have been described in WO 8700836 and in Italian Application No. 21876 A/85 in the Applicant's name.

The isothiouronium salts of formula (II.HB), wherein n is different from 1, are new and can be prepared by treatment of compounds of formula (IV)

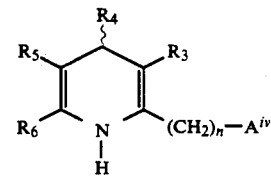

wherein A$^{IV}$ is chlorine, bromine, iodine or a sulfonate ester and R$_3$, R$_4$, R$_5$ and R$_6$ are as above defined, with thiourea and N-alkyl derivatives thereof, using well known methods. Isothiouronium salts are preferably prepared from halides or sulfonates, melting a mixture of the solid reagents or heating their solutions in a solvent selected from dimethylformamide, N-methyl-pyrrolidone, dimethylsulphoxide, ethanol, methanol, acetonitrile, water or mixtures thereof.

1,4-Dihydropyridines of formula (IV) are wellknown form EP 83315, DE 2629892, Synth. Comm 16, 529 1086 and Tethr. Lett. 29, 6335, 1988.

Other isothiouronium salts have been disclosed in EP 225175. Isothioureas of formulae II, Ia$_1$ and Ia$_2$ are new and are an object of the present invention together with processes for the preparation thereof.

Both isothioureas of formula Ia$_1$, Ia$_2$ and/or isothiouronium salts thereof, and thiols and/or C$_1$-C$_{24}$-acylthioesters thereof of formula I (A=SH, C$_1$-C$_{24}$-acyl-S), when reacted with electrophilic species of formula R$_2$-φ, produce compounds of formula I, wherein A is a SR$_2$ group.

The preferred electrophilic species of formula $R_2\phi$ are selected from: a) a diazonium salt wherein $\phi$ is a diazonium group and $R_2$ is an aryl and/or heteroaryl radical; b) as substituted or unsubstituted alkyl halide and/or sulphonate of a suitable substituted or unsubstituted alcohol wherein $R_2$ is an alkyl residue as above defined containing also 3-membered heterocyclic rings such as oxyrane, thiirane, azyridien, N-$(C_1$-$C_6)$-alkylazyridine and $\phi$ is a halogen (Cl, Br, I) or a suitable sulfonate residue such as $CH_3SO_3$—, $C_6H_5SO_3$—, p-methyl-$C_6H_4SO_3$—, or camphosulfonate or trifluoromethanesulphonate ($F_3C$—$SO_3$); c) a Michael acceptor wherein $R_2$ is a $(C_2$-$C_5)$-alk-1-ene or a $(C_1C_6)$alk-1yne and $\phi$ is the activating residue selected from —$NO_2$, —$C\equiv N$, —$CONH_2$, —$CO_2R_{31}$, —$CO(C_1$-$C_4)$-alkyl, —$COC_6H_5$, —$C_6H_5$-$(C_1$-$C_4)$-alkyl-CO— groups.

Said reactions of thiols or masked thiols of formula I with electrophiles are preferably carried out in the presence of bases and under inert gas atmosphere to avoid disulfide by-product formation. The amounts of the bases range from catalytic to stoichiometric amounts or higher when H-$\phi$ acid are released during the reaction; preferably a base excess is used. Preferred bases are organic base such as a tertiary amine, e.g. triethylamine, diazabicyclononene, diazabicycloundecene or an aromatic amine, e.g. pyridine, an alkyl-substituted pyridine, tetramethyl-pyridine, or an anionic ion-exchange resin or, more preferably, an inorganic base e.g. an alkali or an alkali-earth oxide, hydroxyde, carbonate or bicarbonate or $(C_1$-$C_5)$-alcoholate. The base can be used as a solid material for in a diluted solution in media such as water, $(C_1$-$C_5)$-alcohols, dioxane, tetrahydrofuran, $(C_1$-$C_3)$-glycols and mixtures thereof. Ammonia and its solution in the same media can also be use. Most preferably, such reactions with electrophiles are carried out using "phase transfer" conditions, so that the base may be used as a solid and not necessarily in solution. The preferred solvents are those immiscible with water that were previously used during salification and resolution steps. The reaction temperatures range from room temperature to the solvent reflux temperature. The reaction times can range form few minutes to several days, but usually do not exceed a period from six to eight hours at room temperature. When, in a compound of formula I, one or both of $R_3$ and $R_5$ are allyl esters, they may be selectively cleaved by "transfer hydrogenolysis" under very mild conditions by treatment with an ammonium and/or alkylammonium salt in the presence of a phosphine and a hydrogen transfer catalyst.

Ammonium formate is the preferred salt; triphenyl and tributyl phosphine are particularly useful.

Preferred transfer catalyst is palladium (Pd) on carbon, finely dispersed in a concentration from 2 to 15%. Preferred solvents are $(C_1$-$C_5)$-alcohols, acetonitrile and other aliphatic nitriles; ethers such as tetrahydrofuran, dioxane, dimethoxyethane, amides such as dimethylformamide, formamide, water and mixtures thereof. The reaction may be carried out at a temperature ranging from 0° C. to the solvent reflux temperature in a time ranging from some minutes to several hours.

The hydrolysis of these allyl esters occurs in almost theoretical yields.

When desired, each of these dihydropyridine acids can be transformed into another compound of formula I by esterification with a suitable alcohol, using known methods. When $R_3$ and $R_4$ are carboxyester groups which may be selectively hydrolized (e.g. one is an allyl ester and the other one is a t-butyl or trichloroethylester) enantiomerically pure 1,4-dihydropyridines may be converted into the specular enantiomer, as shown in the above scheme, by suitable sequence of selective cleavage and reaction with appropriate alcohols, either racemic or optically pure.

A further advantage of the present invention is the preparation of single enantiomers of diastereoisomeric dihydropyridines when, according to this procedure, enantiomeric dihydropyridines having free carboxy groups at positions " and/or 5 are reacted with optically active alcohols or amines.

Sulfonium salts of formula I wherein A is

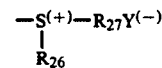

may be prepared by treatment of a compound of formula I, wherein A is more preferably —$SR_2$, with an excess of a $(C_1$-$C_6)$-alkyl halide or a phenyl-$(C_1$-$C_6)$-aralkyl halide or with a trialkyloxonium tetrafluoroborate of formula $[(R_{26})_2O^{(+)}R_{27}]BF_4^{(-)}$ being $R_{26}$ and $R_{27}$ as above defined.

Preferred reaction conditions include the use of an excess of the selected halide int he presence or not of an inert solvent. Suitable solvents are dioxane, tetrahydrofuran, dimethoxyethane, an aromatic hydrocarbon such as benzene, toluene, amides such as dimethylformamide, N-methylpyrrolidone or esters such as ethyl acetate and mixtures thereof; preferred temperatures range from the room temperature to the reflux temperature of the mixture.

The use of slight molar excess of trialkyloxonium tetrafluoroborates in dimethoxyethane, at room temperature for several hours is particularly preferred; often the sulfonium slat separates as a crystalline product from the reaction mixture.

Enantiomerically pure 1,4-dihydropyridines of formula I wherein A is hydrogen are obtained by reacting one of said sulphonium salts with an hydride selected from sodium, lithium, zinc or tetraalkylammonium (e.g. tetrabutylammonium) borohydride, tri-(tert-butyl) aluminium hydride, diisobutyl-aluminium hydride or lithium aluminium hydride.

Desulfuration of sulphonium salts is a very selective process that occurs under extremely mild conditions; the choice of solvent and the preferred experimental conditions depend on the selected hydride.

Anhydrous solvents such as 1,2-dimethoxyethane, tetrahydrofuran, diethylether, dioxane, toluene and benzene or mixtures thereof are preferably used with aluminium hydrides, while in the case of borohydrides additional solvents can be conveniently used, for instance: aprotic dipolar solvents such as N,N-dimethylformamide, dimethylsulphoxide, N-methyl-pyrrolidone, sulpholane, $(C_1$-$C_5)$-alcohols, ethyleneglycol, polyethyleneglycols, halogenated solvents such as 1,2-dichloroethane and dichloromethane or mixtures thereof. Preferably a molar excess of the hydride is used, at a temperature form 0° C. to reflux temperature. The use of borohydrides at room temperature, for a reaction time ranging from few min. to 4 hrs. is preferred.

Hydride-promoted removal of the sulphonium residue occurs under particularly mild and selective conditions without affecting the 1,4-dihydropyridine, whose reactivity towards hydrides is known (see for example A. Sauvins et al. Heterocycles 27, 291, 1988) or other possible reducible groups.

For example, (+) and (−) enantiomers of dimethyl-]6-methyl-5-carbomethoxy-3-carboethoxy-4-(3-nitrophenyl-1,4-dihydropyridine-2-yl]-methyl-ethyl-sulphonium tetrafluoroborate are quantitatively desulphurated to give the corresponding crystalline (+) and (−) enantiomers of 2,6-dimethyl-3-carboethoxy-5-carbomethoxy-4-(3-nitrophenyl)-1,4-dihydropyridine by reaction with sodiumborohydride in dimethylformamide at 5°–10° C.

Alternative use of classic reagents, as Ni-Raney or Na/Hg amalgam, in the desulphuration process is expected to be less useful, duet to the concomitant reduction of nitro groups to amino groups.

However, when the phenyl group $R_4$ of the sulphurated compounds of formula I is not substituted by nitro or azido groups, classic desulfurating agents such as Ni-Raney or Na/Hg amalgams can also be sued for the preparation of enantiomerically pure 1,4-dihydropyridine of formula I wherein A is hydrogen. Sometimes the reduction of the nitro group of the $R_4$ substituent might be synthetically useful since the formed amino group could be transformed into other groups via diazonium salts. Preferred concentrations of Na in Hg amalgams range from 2 to 10%; preferred rations between sulphurated substrate and desulfurating reagents (ni-Raney) or Na/Hg range from equimolar to 520 times molar excess.

Anhydrous solvents used with Na/Hg amalgams include ($C_1$–$C_5$)-alcohols, tetrahydrofuran, 1,2-dimethoxyethane, dioxane, dimethylformamide, N-methylpyrrolidone; in the case of Ni-Raney also water and acetone or mixtures thereof can be used; the reaction temperature ranges from 40° C. to the reflux temperature of the mixture. Even through a series of side-reactions (including saturation of olefins and of aromatic rings, alcohol formation from ketones, rearrangement and condensation reactions) have been reported during the desulfuration with Ni-Raney (see for instance G. R. Pettit, "Desulfuration with Raney Nickel" in Organic Reactions, vol. XII, pag. 360362, R. E. Krieger Publ. Co. Halabar, Fla., 1975), now side reactions such as oxydation or dimeriztion of the 1,4-dihydropyridine ring or reduction to tetrahydro- or hexahydropyridines, could be observed.

Surprisingly, nitrovinyl groups of compounds of formula I (when $R_5$ is a $NO_2$) are substantially inert to the reductive action of desulfurating agents such as Ni-Raney or Na/Hg. The substantial stability of said nitrovinyl group is remarkable when compared with that of ortho-, meta- or para- nitro groups possibly present in the $R_4$ phenyl substituent that, on the contrary, are partially or completely reduce to amino groups.

It is also remarkable that, in enantiomers of formula i, different reduction rates to amino are observed along the o-, m- and p- nitrophenyl $R_4$ substituents, ranging from a maximum to a minimum rate changing the nitro group position form para- to ortho-. After short reaction times, the desulfuration of C-4 m- or o-nitrophenyl substituted compounds may proceed in a 40–50% extend without noticeable reduction of the nitro groups.

The examples reported herebelow further illustrate the present invention. In said examples the following abbreviations are used: MeOH=methanol, EtOH=ethanol, AcOEt=ethyl acetate, AcOH=acetic acid, THF=tetrahydrofuran, DMF=dimethylformamide, DMSO=dimethylsulphoxide, at reflux=at the reflux temperature.

PREPARATION 1

A solution of (±)-2-chloromethyl-3-carboethoxy-5-nitro-4-(m-nitrophenyl)-6-methyl-1,4-dihydropyridine (g 1.1), thiourea (g 0.23) in EtOH (ml 10) is heated to reflux for two hours.

After cooling, the crystalline precipitate of (±)-S-[(6-methyl-3-carboethoxy-5-nitro-4-(m-nitrophenyl)-1,4-dihydropyridine-2-yl)-methyl]-isothiouronium chloride (g 1.26, m.p. 198°–200° C.) is collected by filtration.

PREPARATION 2

A solution of (±)-2-chloromethyl-3,5-dicarboethoxy-4-(3-nitrophenyl)-6-methyl-1,4-dihydropyridine (g 6) and 3,4,5,6-tetrahydro-2-mercaptopyrimidine (g 1.8) in MeOH (ml 50) is heated at reflux for two hours. After cooling to room temperature, g 7 of (±)-2-[(1,4,5,6-tetrahydropyrimidin-2-yl)thio-]-methyl-3,5-dicarboethoxy-6-methyl-4-(3-nitrophenyl)-1,4-dihydropyridine hydrochloride (m.p. 271°–219° C.) are obtained.

PREPARATION 3

A solution of (±)-2-chloromethyl-3-carbomethoxy-5-carboethoxy-4-(3-trifluoromethylphenyl)-6-methyl-1,4-dihydropyridine (g 1.5) and 2-imidazolidinthione (g 0.5) in benzene (ml 20) is heated to reflux for 6 hours. After cooling, the precipitate of (±)-2-[(4,5-dihydroimidazol-2-yl)thio-]-methyl-3-carbomethoxy-5-carboethoxy-4-(3-trifluoromethylphenyl-6-methyl-1,4-dihydropyridine hydrochloride (m.p. 190°–192° C.) is collected by filtration.

PREPARATION 4

A mixture of (±)-2-chloromethyl-3,5-dicarboethoxy-4-(3-nitrophenyl)-6-methyl-1,4-dihydropyridine (g 6), thiourea (g 1.2)and EtOH (ml 60) is heated to reflux of three hours. After cooling to room temperature, 4.8 g of (±)-S-[(6-methyl-3,5-dicarboethoxy-4-(3-nitrophenyl)-1,4-dihydropyridine-2-yl)-methyl]-isothiouronium chloride (m.p. 219°–220° C.) are obtained.

PREPARATION 5

A mixture of ethyl 4-chloro-3-oxobutanoate (12.1 g), benzo-[c]-furazan-4-aldehyde (10 g), acetic acid (ml 0.2) and benzylamine (ml 0.37) is stirred for 24 hours at room temperature and is then diluted with acetonitrile (ml 95). After addition of 8.5 g of methyl 3-aminocrotonate, the solution is heated for three hours to 60° C., cooled to 35° C. and then treated with g 4.8 of p-toluenesulphonic acid. After further 30 minutes, the stirred solution is treated with 2 ml of a 28% solution of ammonium hydrate, concentrated under vacuum to ⅓ of its volume and finally diluted with water (150 ml). After extraction with ethyl acetate (3×40 Ml) and usual workup, by evaporation of the solvent and crystallization, 18 g of 2-chloromethyl-6-methyl-3-carboethoxy-5-carbomethoxy-4 -(benzo-[c]-furazan-4-yl)-1,4-dihydropyridine are obtained m.p. 121°–122° C. (from MeOH); m.p. 92°–94° C. (from $Et_2O$).

In the same way, by reaction of benzo-[c]-furazan-4-aldehyde with a suitable alkyl 4-chloro-3-oxobutanoate and a suitable enamine selected from alkyl 3-aminocrotonate, 3-aminocrotonitrile and 2-amino-1nitroprop-1-ene, the following compounds are obtained:

2-chloromethyl-6-methyl-3-carboethoxy-5-cyano-4-(benzo-[c]-furazan-4-yl)-1,4-dihydropyridine, m.p. 125°–126° C.;

2-chloromethyl-6-methyl-3-carbomethoxy-5-isopropoxycarbonyl-4-(benzo-[c]-furazan-4-yl)-1,4-dihydropyridine m.p. 146°–148° C.;

2-chloromethyl-6-methyl-3-carboethoxy-5-nitro-4-(benzo-[c]-furazan-4-yl)-1,4-dihydropyridine;

2-chloromethyl-6-methyl-3-carbomethoxy-5-allyloxycarbonyl-4-(benzo-[c]-furazan-4-yl)-1,4-dihydropyridine.

A solution of 2-chloromethyl-6-methyl-3-carbomethoxy-5-allyloxycarbonyl-4-(benzo-[c]-furazan-4-yl)-1,4-dihydropyridine (g 2.4) and thiourea (b 0.6) in methanol (ml 40) is heated at reflux for 4 hours. After cooling a solid of (+)-S-[(6-methyl-3-carbomethoxy-5-allyloxycarbonyl-4-(benzo-[c]-furazan-4-yl)-1,4-dihydropyridine-2-yl)methyl]-isothiouronium chloride (2.23 g) is separated, filtered and dried under vacuum.

PREPARATION 6

Using the aldehydes 5-formylbenzo-[b]-1,4-dioxane and 6-formylbenzo-[c]-1,4-dioxane in the procedure of preparation 5, the following compounds are prepared:

2-chloromethyl-6-methyl-3-carboethoxy-5-tert-butoxycarbonyl-4-(benzo-[b]-1,4-dioxane-5-yl)-1,4-dihydropyridine, m.p. 128°–130° C.;

2-chloromethyl-6-methyl-3-carboethoxy-5-tert-butoxycarbonyl-4-(benzo-[c]-1,4-dioxan-6-yl)-1,4-dihydropyridine, m.p. 115°–°117° C.;

2-chloromethyl-6-methyl-3-carboethoxy-5-carbomethoxy-4-benzo-[b]-1,4-dioxan-5-yl)-1,4-dihydropyridine, m.p. 121°–122° C.;

2-chloromethyl-6-methyl-3-carboethoxy-5-tert-butoxycarbonyl-4-(benzo-[c]-1,4-dioxan-6-yl)-1,4-dihydropyridine, m.p. 137°–139° C.;

2-chloromethyl-6-methyl-3-carboethoxy-5-cyano-4-(benzo-[b]-1,4-dioxan-5-yl)-1,4-dihydropyridine, m.p. 130°–132° C.

Under inert gas atmosphere, a stirred suspension of 2-chloromethyl-6-methyl-3-carboethoxy-5-cyano-4-(benzo-[b]-1,4-dioxan-5-yl)-1,4-dihydropyridine (3.7g) and thiourea (0.82 g) in 5 ml of N-methylpyrrolidone is heated to 95°–105° C. for 20 minutes. The clear solution is cooled, diluted with EtOH (20 ml) to separate 3.8 g of (±)-S-[(6-methyl-5-cyano-4-(benzo-[b]-1,4-dioxan-5-yl)-3-carboethoxy-1,4-dihydropyridin-2-yl)-methyl]isothiouronium chloride, m.p. 235°–237° C.

PREPARATION 7

A solution of ethyl α-(2-chloroacetyl)-3-chlorocinnamate in EtOH (50 ml) and a 3-cyano-3-aminopropenoic ester (for ex. ethyl 3-cyano-3-aminopropenoate g 1.45) is heated to reflux for 3 hours, cooled to 40° C. and treated with a solution of p-toluenesulphonic acid (g 1.9) in EtOH (10 ml). After 2 hours the mixture is concentrated to small volume, diluted with water and extracted with AcOEt (3×25 ml). The organic phases are combined, washed with water, 5% aqueous $K_2CO_3$, water, dried and evaporated to dryness. By chromatography on silica gel column ($SiO_2$, 80 g, eluent AcOEt hexane 3/7) 3.1 g of 2-chloromethyl-6-cyano-4-(3-chloroephenyl)-3,5-dicarboethoxy-1,4-dihydropyridine are obtained.

A stirred mixture of the compound with thiourea (0.8 g) in 5 ml DMF is heated to 95°–105° C. for 30 minutes, cooled, diluted with EtOH (15 ml) to obtain a crystalline precipitate of (±)-S-[(6-cyano-4-(3-chlorophenyl)-3,5-dicarboethoxy-1,4-dihydropyridin-2-yl)-methyl]-isothiouronium chloride.

PREPARATION 8

Using ethyl 3,3-diethoxymethyl-3-amino-propenoate and ethyl 3-ethoxycarbonyl-3-amino-propenoate instead of ethyl 3-cyano-3-amino-propenoate in the procedure of preparation 7, the following compounds are prepared:

2-chloromethyl-6-diethoxymethyl-4-(3-chlorophenyl)-3,5-dicarboethoxy-1,4-dihydropyridine;

2-chloromethyl-6-ethoxycarbonyl-4-(3-chlorophenyl)-3,5-dicarboethoxy-1,4-dihydropyridine;

(±)-S-[(6-diethoxymethyl-4-(3-chloroephenyl)-3,5-dicarboethoxy-1,4-dihydropyridin-2-yl)-methyl]-isothiouronium chloride;

(±)-S-[(6-ethoxycarbonyl-4-(3-chloroephenyl)-3,5-dicarboethoxy-1,4-dihydropyridin-2-yl)-methyl]-isothiouronium chloride;

PREPARATION 9

Using in the procedure of preparation 5 the aldehydes of the group consisting of benzaldehyde, α-pyridinyl carboxyaldehyde and 2-thiophene carboxyaldehyde and an enamine of the group consisting of 1-acetyl-2-aminopropene, 1-benzoyl-2-aminopropene and 1-(2-phenylacetyl)-2-aminopropene instead of methyl-3-aminocrotonate, the following compounds are prepared:

-2-chloromethyl-6-methyl-3-carboethoxy-5-acetyl-4-phenyl-1,4-dihydropyridine;

-2-chloromethy-6-methyl-3-carboethoxy-5-acetyl-4-(2-thienyl)-1,4-dihydropyridine;

-2-chloromethy-6-methyl-3-carboethoxy-5-benzoyl-4-(2-thienyl)-1,4-dihydropyridine;

-2-chloromethy-6-methyl-3-carboethoxy-5-(2-phenylacetyl)-4-(pyridin-2-yl)-1,4-dihydropyridine.

PREPARATION 10

According to the procedures of the preparations from 1 to 7, by treatment of a (±)-2-chloromethyl-1,4-dihydropyridine with thiourea and/or a N-alkylthiourea selected from N-methylthiourea, N,N'-dimethylthiourea, 2-imidasolidinthione, 1-methyl-2-imidazolidinthione, 3,4,5,6-tetrahydro-2-mercaptopyrimidine, the following racemates are obtained:

-S-[(6-methyl-5-cyano-4-(3-nitrophenyl)-3-carboethoxy-1,4-dihydropyridin-2-yl)methyl]-isothiouronium chloride, m.p. 198°–200° C., (isothiourea, free base, m.p. 123°–125° C.);

-S-[(6-methyl-5-acetyl-4-phenyl-3-carboethoxy-1,4-dihydro-pyridine-2-yl)methyl]-isothiouronium chloride;

-S-[(6-methyl-5-carbomethoxy-4-(3-nitrophenyl)-3-carboethoxy-1,4-dihydropyridin-2-yl)methyl]-isothiouronium chloride, m.p. 173°–176° C.; (isothiourea free base m.p. 131°–133° C.);

-S-[(6-methyl-5-carbisopropoxy-4-(3-nitrophenyl)-3-carboethoxy-1,4-dihydropyridin-2-yl)methyl]-isothiouronium chloride;

-S-[(6-methyl-3,5-dicarboethoxy-(2-chlorophenyl)-1,4-dihydropyridin-2-yl)methyl]-isothiourea;

-S-[(6-methyl-5-carboethoxy-3-carboethoxy-(3-chlorophenyl)-1,4-dihydropyridin-2-yl)methyl]-isothiouronium chloride;

-S-[(6-methyl-3,5-dicarboethoxy-4-(2-trifluoromethylphenyl)-1,4-dihydropyridin-2-yl)methyl]-isothiouronium chloride;

-S-[(6-methyl-5-carbomethoxy-3-carboethoxy-4-(2-trifluoromethylphenyl)-1,4-dihydropyridin-2-yl)methyl]-N-methylisothiouronium chloride;

-S-[(6-methyl-3-carboethoxy-5-cyano-4-(2-trifluoromethylphenyl)-1,4-dihydropyridin-2yl)methyl]isothiouronium fumarate;

-S-[(6-methyl-5-carbomethoxy-3-carboethoxy-4-(4-fluorophenyl)-1,4-dihydropyridin-2-yl)methyl]-N,N'-dimethyl isothiouronium chloride;

-S- [(6-methyl-5-carbomethoxy-3-carboethoxy-4-(3-trifluoromethylphenyl)-1,4-dihydropyridin-2-yl)methyl]isothiouronium chloride;

-S-[(6-methyl-5-carbomethoxy-3-carboethoxy-4(4-nitrophenyl)-1,4-dihydropyridin-2-yl)methyl]-isothiouronium chloride;

-S-[(6-methyl-5-carbomethoxy-3-carboethoxy-4-(2-nitrophenyl)-1,4-dihydropyridin-2-yl)methyl]-isothiouronium chloride;

-2-[(1,4,5,6-tetrahydropyrimidin-2-yl)thio]-methyl-5-carbomethoxy- 3-carboethoxy-6-methyl-4-(3-nitrophenyl)1,4-dihydropyridine hydrochloride, m.p. 240°-242° C.;

-2-[(4,5-dihydroimidazol-2-yl)thio]methyl-3-carbomethoxy-5-carbomethoxy-4-(3-trifluoromethylphenyl)-6-methyl-1,4-dihydropyridine, m.p. 190°-192° C.;

-2-[(4,5-dihydroimidazol-2-yl)thio]methyl-3,5-dicarboethoxy-4(3-nitrophenyl)-6-methyl-1,4-dihydropyridine hydrochloride, m.p. 211°-213° C.;

-2-[(1,4,5,6-tetrahydropyrimidin-2-yl)thio]methyl-5-tert-butoxycarbonyl-3-ethoxycarbonyl-4-(3-nitrophenyl)-6-methyl-1,4-dihydropyridine.HCl, m.p. 203°-204° C.;

-2-[(1-methyl-4,5-dihydroimidazol-2-yl)thio]methyl-3,5-dicarboethoxy-4-(3-chlorophenyl)-6-methyl-1,4-dihydropyridine hydrochloride;

-2-[(1-methyl-4,5-dihydroimidazol-2-yl)thio]methyl-3-carboethoxy-5-carbomethoxy-4-(3-cyanophenyl)-6-methyl-1,4-dihydropyridine hydrochloride;

-2-[(1-methyl-4,5-dihydroimidazol-2-yl)thio]methyl-3-carboethoxy-5-carbomethoxy-4-(4-chlorophenyl)-6-methyl-1,4-dihydropyridine hydrochloride;

-2-[(1-methyl-4,5-dihydroimidazol-2-yl)thio]methyl-3-carboethoxy-5-carbomethoxy-4-(2,3-dichlorophenyl)-6-methyl-1,4-dihydropyridine hydrochloride;

-2-[(4,5-dihydroimidazol-2-yl)thio]methyl-3,5-dicarboethoxy-4-(3-chlorophenyl)-6-methyl-1,4-dihydropyridine hydrochloride;

-2-[(4,5-dihydroimidazol-2-yl)thio]methyl-3-carboethoxy-5-nitro-4-(3-trifluoromethylphenyl)-6-methyl-1,4-dihydropyridine hydrochloride;

-S-[(6-fluoromethyl-3,5-dicarbomethoxy-4-(3-nitrophenyl- 1,4-dihydropyridin-2-yl)methyl]-isothiouronium chloride;

-S-[(6-formyl-3,5-dicarboethoxy-4-(3-chlorophenyl)-1,4-dihydropyridin-2-yl)-methyl]-isothiouronium chloride;

-S-[(6-diethoxymethyl-3-carboethoxy-4-(3-chlorophenyl)1,4-dihydropyridin-2-yl)methyl]-isothiouronium chloride;

-S-[(6-cyano-3-carboethoxy-5-(2-methoxyethoxy)-carbonyl-4-(3-thienyl)-1,4-dihydropyridin-2yl)methyl]-isothiouronium chloride;

-S-[(6-cyano-5-carboethoxy-3-isopropoxycarbonyl-4-benzo[b]-1,4-dioxan-5-yl)-1,4-dihydropyridin-2-yl)methyl]-isothiouronium chloride;

-S-[(6-cyano-3,5-dicarboethoxy-4-(benzo-[c]-furazan-4-yl)-1,4-dihydropyridin-2-yl)-methyl]-isothiouronium chloride;

-S-[(6-cyano-3,5-dicarbomethoxy-4-(3-trifluoromethylphenyl)-1,4-dihydropyridin-2-yl)methyl]-isothiouronium chloride;

-S-[(6-methyl-3-carboethoxy-5-allyloxycarbonyl-4-(3-nitrophenyl)-1,4-dihydropyridin-2-yl)methyl]-isothiouronium chloride;

-S-[(6-methyl-3carbomethoxy-5-(2-butenoxycarbonyl)-4-(2-chlorophenyl)-1,4-dihydropyridin-2-yl)methyl]-isothiouronium chloride;

-S-[(6-methyl-3carboethoxy-5-tert-butoxycarbonyl-4-(3-nitrophenyl)-1,4-dihydropyridin-2-yl)methyl]-isothiouronium chloride;

-S-[(6-methyl-3-carbomethoxy-5-allyloxycarbonyl-4-(3-nitrophenyl)-1,4-dihydropyridin-2-yl)methyl]-isothiouronium chloride;

-S-[(6-methyl-3-allyloxycarbonyl-5-carbomethoxy-4-(3-nitrophenyl)- 1,4-dihydropyridin-2-yl)methyl]-isothiouronium chloride;

-S-[(6-methyl-3,5-diallyloxycarbonyl-4-(3-nitrophenyl)-1,4-dihydropyridin-2-yl)methyl]-isothiouronium chloride;

-S-[(6-methyl-3-carbomethoxy-5-allyloxycarbonyl-4-(2,3-dichlorophenyl)-1,4-dihydropyridin-2-yl)methyl]isothiouronium chloride;

-S-[(6-methyl-3-carboethoxy-5-acetyl-4-(2-thienyl)-1,4-dihydropyridin-2-yl)methyl]-isothiouronium chloride;

-S-[(6-methyl-3-carboethoxy-5-benzoyl-4-(2-thienyl)-1,4-dihydropyridin-2-yl)methyl]-isothiouronium chloride;

-S-[(6-methyl-3-carboethoxy-5-(2-phenylacetyl)-4-(pyridin-2-yl)-1,4-dihydropyridin-2-yl)methyl]-isothiouronium chloride;

-S-[(6-methyl-3-carboethoxy-5-carbomethoxy-4-(benzo-[c]-furazan-4-yl)-1,4-dihydropyridin-2yl)methyl]-isothiouronium chloride;

-S-[(6-methyl-3-allyloxycarbonyl-5-carbomethoxy-4-benzo-[c]-furazan-4-yl)-1,4-dihydropyridin-2-yl)methyl]-isothiouronium chloride.

EXAMPLE 1

A suspension of (+)-S-[(6-methyl-3,5-dicarboethoxy-4-(3-nitrophenyl)-1,4-dihydropyridin-2-yl)methyl]-isothiouronium chloride (g 1) in AcOEt (ml 20) and water (ml 10) is added in 30' with sodium bicarbonate (g 0.1) at room temperature and under vigorous stirring. The phases are separated and the aqueous phase is extracted with AcOEt (2×5 ml). The organic phases are combined, washed with a NaCl saturated solution and fired on $Na_2SO_4$. After evaporation of the solvent and crystallization from $Et_2O$, 0.9 g of (±)-S-[(6-methyl-3,5-dicarboethoxy-4-(3-nitrophenyl)-1,4-dihydropyridin-2yl)methyl]-isothiourea are obtained (m.p. 119°-121° C.).

EXAMPLE 2

A mixture of (±)-S-[(6-methyl-3,5-dicarboethoxy-4-(m-nitrophenyl-1,4-dihydropyridin-2yl)methyl]-isothiourea (g 21), 0,0'-dibenzoyl-D-tartaric acid (g 18) and acetonitrile (ml 600) is heated tot he reflux temperature for one hour. After spontaneous cooling at room temperature, the solution is cooled to 0° C. and stirred for one hour to separate a solid that is filtered and washed with acetonitrile (ml 40). Said crystalline material [g 15.8, m.p. 158°-160° C.; $[\alpha]_d = +80.8°$ $[\alpha]_{578} = +85.51°$

[α]₅₄₆=+103.7° (c=1.1, MeOH)] is crystallized by heating in acetonitrile (ml 240) for one hour at the reflux temperature. The solution is cooled to room temperature and stirred for one hour at 0° C., to separate 14.5 g of (+)-S-[(6-methyl-3,5-dicarboethoxy-4-(3-nitrophenyl)-1,4-dihydropyridin-2-yl)methyl]-isothiouronium 0,0'-dibenzoyl-D-tartrate [m.p. 161°-162° C.; [α]$_D$=+81.5°; [α]₅₇₈=+85.4°; [α]₅₄₆=+102.1°, c=1.4, MeOH].

The mother liquors from the first crystallization are evaporated to dryness under vacuum. The residue is partitioned between AcOEt (ml 250) and 1.1% aqueous solution of sodium bicarbonate )2-50 ml), by stirring for 1.5 hours. After separation and elimination of the aqueous phase, the organic phase is washed with brine, dried (Na₂SO₄) and evaporated to dryness. A stirred solution of the crude residue (g 14.15) and of 0,0'-dibenzoyl-L-tartaric acid in acetonitrile (590ml) is maintained for 6 hours at room temperature and then for a night at 4° C. to separate a precipitate, that is filtered and washed with cold acetonitrile (ml 50). The crystalline material [g 15.06, m.p. 156°-158° C.; [α]$_D$=−76.8°; [α]₅₄₆=−91.4°, c=1.4, MeOH] is dissolved in hot acetonitrile (ml 230). The stirred solution is cooled at room temperature, maintained for 6.5 hours at 4° C. to separate g 12.1 of: (-)-S-[(6-methyl-3,5-dicarboethoxy-4-(3-nitrophenyl-1,4-dihydropyridin-2-yl)methyl]-isothiouronium 0,0'-dibenzoyl-L-tartrate, (m.p. 160°-161° C.; [α]$_D$ = −72.4°, [α]₅₇₈=−77.4°;[α]₅₄₆=−92.9°, C=1,6, MeOH].

The chiral isothioureas are obtained as free bases by treatment of chiral isothiouronium salts with bases. Thus sodium bicarbonate (g 0.105) is added to a stirred suspension of the 0,0'-dibenzoyltartrate isothiouronium salt (g 1) in a biphasic water/AcOEt (1:1, 40 ml) mixture. After 10 minutes the aqueous phase is separated, washed with AcOEt (2×5 ml) and discarded The organic phases are combined, washed with 5% aqueous NaHCO₃ solution (2×5 ml) and dried. The residue is triturated with Et₂0 (ml 7) to give (+)-S-[(6-methyl-3,5-dicarboethoxy-4-(3-nitrophenyl)-1,4-dihydropyridin-2-yl) methyl]-isothiourea [g 0.85; m.p. 124°-126° C.; [α]$_D$=−69.4°, [α]₅₇₈=−73.0°; [α]₅₄₆=−83.5°; c=1.3, CH₂Cl₂).

The optical purity of the single enantiomers, that is ascertained by 1H NMR analysis in the presence of the chiral tris-[3-(trifluoromethylhydroxymethylene)-d-camphorate]-praseodimium (III) lantanide reagent, is >98%.

EXAMPLE 3

A KHCO₃ (g 106.3) aqueous solution (1100 ml) and 28% aqueous ammonia (35ml) are added to a stirred suspension of (±)-S-[(6-methyl-5-carbomethoxy-3-carboethoxy-4-(3-nitrophenyl-1,4-dihydropyridin-2-yl)methyl]-isothiouronium chloride (g 500) in AcOEt (5000 ml) cooled at +35° C. 30 Minutes after, the organic phase is separated, washed with brine (2×800 ml), dried on Na₂SO₄ (g 400) and filtered.

L-(+)-mandelic acid (98%; g 164.8) is then added to the stirred solution in AcOEt of the rac-isothiourea, thus obtained as free base, to give, 4 hours later a crystalline solid that is filtered (g 260; m.p. 164°-166° C.; [α]$_D$=+20.9°, c=2.1, DMR) and crystallized from EtOH (1300 ml, 50° C., 1 h) to give 247 g of (-30 )-S-[(6-methyl-5-carbomethoxy-3-carboethoxy-4-(3-nitrophenyl)-1,4-dihydropyridin-2-yl)methyl]-isothiouronium L-mandelate (m.p. 166°-168° C.), [α]$_D$=+20.9°, [α]₅₄₆=+19.9°, c=2.3, DMF).

The mother liquors from the first crystallization from ethyl acetate (5000 ml), are concentrated to half volume under vacuum, and under stirring at ±35° C. are treated with a KHCO₃ (g 67) aqueous solution (ml 700) and then with 28% aqueous ammonia (ml 30). 30 minutes later the organic phase is separated, washed with brine (2×350 ml), dried on Na₂SO₄ (g 250) and filtered.

Following addition of D-(−)-mandelic acid (98%; g 96) thereto and stirring for 6 hours at room temperature give a solid (g 282; m.p. 163°-166° C.; [α]$_D$=−19.0°, c=2.7, DMF) that is crystallized from EtOH (1300 ml; 50° C.; 1 h) to give 260 g of (−)-S-[(6-methyl-5-carbomethoxy-3-carboethoxy-4-(3-nitrophenyl)-1,4-dihydropyridin-2-yl)methyl]-isothiouronium D-mandelate, (m.p. 165°-167° C.; [α]$_D$=−21.3°, [α]₅₇₈=−21.3° [α]₅₄₆=−20.8°, c=2.2, DMF). The free bases:
(+)-S-[(6-methyl-5-carbomethoxy-3-carboethoxy-4-(3-nitrophenyl)-1,4-dihydropyridin-2-yl)methyl]isothiourea (m.p. 122°-124° C.; [α]$_D$=+64.2°; [α]₅₇₈=67.3+; [α]₅₄₆=75.8°; b=2.0 CH₂Cl₂) and its (-)enantiomer (m.p. 123°-124°0 C; [α]$_D$=−64.4° [α]₅₇₈=−55.9°; [α]₅₄₆=−75.6°, c=2.0 CH₂Cl₂) are obtained by L- and D-mandelate isothiouronium salts using the procedure of example 2 (AcOEt/H₂O/NaHCO₃).

EXAMPLE 4

Using BOC-L-phenylalanine and BOC-L-leucine, as resolving agents of (±)-S-[(6-methyl-5-carbomethoxy-3-carboethoxy-4-(3-nitrophenyl)-1,4-dihydropyridin-2-yl)methyl]-isothiourea, in the procedure of example 2, the following isothiouronium salts are obtained:
(+)-S-[(6-methyl-5-carbomethoxy-3-carboethoxy-4-(3-nitrophenyl)-1,4-dihydropyridin-2-yl)methyl]-isothiouronium L -Boc-phenylalanylate (m.p. 155°-158° C.; [α]$_D$=−25.3°, [α[₅₇₈=+27.6° [α]₅₄₆=+34.8°; c=2.1, MeOH);
(+)-S-[(6-methyl-5-carbomethoxy-3-carboethoxy-4-(3-nitrophenyl)-1,4-dihydropyridin-2-yl)-isothiouronium L-Boc-leucinate (m.p. 136°-137° C., [α]$_D$=+2.3° [α]₅₇₈=+3.2° [α]₅₄₆=6.7°; c=2.5, MeOH).

EXAMPLE 5

Powdered KHCO₃ (g 17) and water (ml 280) are added to a stirred suspension of: (±)-S-[(6-methyl-5-nitro-4 -(3-nitrophenyl)-3-carboethoxy-1,4-dihydropyridin-2-yl)-methyl]isothiouronium chloride (g 70) in EtOH (ml 280), cooled at +10°/+20° C. One hour after, at room temperature (23°-25° C.), the solid material is filtered and washed with water (300 ml), obtaining (±)-S-[(6-methyl-5-nitro-4-m-nitrophenyl)-3-carboethoxy-1,4-dihydropyridin-2-yl)-methyl] isothiourea (64 g, m.p. 143°-144° C.), that is added to a solution of L-(+)-mandelic acid (b 24) in acetonitrile (ml 800). The mixture is warmed to 40°-50° C. until a clear solution is obtained, that is then filtered, cooled and left for one night at room temperature.

The collected precipitate (g 33.4, m.p. 145°-147° C.; [α]$_D$=−27.5° DMF, c=2.1) is recrystallized from acetonitrile (ml 270) to give g 32.7 of enantiomerically pure (-)-S-[(6-methyl-5-nitro-4-(3-nitrophenyl)-3-carboethoxy-1,4-dihydropyridin-2-yl)methyl]-isothiouronium L -mandelate (m.p. 147°-148° C.; [α]$_D$=−29,5°; [α[₅₇₈=−35.0° c=2.0 in DMF).

The first mother liquors are evaporated to dryness, the crude residue (g 53) is treated in EtOH (ml 200) with KHCO$_3$ (g 10.5) and water (ml 300) to separate g 35.2 of a solid material that is dissolved in a solution of D-(−)-mandelic acid (g 13.3) in acetonitrile (ml 390). After a night at 4° C., the solid obtained (g 36.7; m.p. 146°-147° C.; [α]$_D$=°29°, c=2.0, DMF), is recrystallized from acetonitrile, to give g 35.3 of (+)-S-[(6-methyl-5-nitro-4-(3-nitrophenyl)-3-carboethoxy-1,4-dihydropyridin-2-yl)-methyl]-isothiouronium D-mandelate (m.p. 146°-147° C.; [α]$_D$=+29.0°; [α]$_{578}$=+34.0°; c=1.9 DMF).

EXAMPLE 6

A solution of (±)-S-[(6-methyl-5-cyano-4-(3-nitrophenyl)-3-carboethoxy-1,4-dihydropyridin-2-yl)methyl]-isothiourea (g 37) and L-(+)-mandelic acid (g 13.9) in acetonitrile (ml 400) is stirred for 4 hours at room temperature. One night after, at +4° C., g 10.2 of a solid ([α]$_D$=+128.5°, c=1.2,MeOH) are filtered and the mother liquors are evaporated to dryness under vacuum. A solution of the crude residue in 1,2-dichloroethane (ml 100) is stirred overnight at room temperature to separate a second crystalline crop (g 9.9, [α]$_D$=+119.5°, c=1.3, MeOH). The combined crystals are recrystallized from acetonitrile (ml 100) to give 18.2 g of (+)-S-[(6-methyl-5-cyano-4-(3-nitrophenyl)-3-carboethoxy-1,4-dihydropyridin-2-yl)methyl]-isothiouronium L-mandelate (m.p. 161°-163° C.; [α]$_D$=+129.5°, [α]$_{578}$=+133.5°, [α]$_{546}$=+161.3°, [α]$_{436}$=+460.1°; c=0.97, MeOH: isothiourea free base [α]$_D$=+217.7°, [α]$_{578}$=+235.5°, [α]$_{546}$=+816.9°; CH$_2$Cl$_2$, c=0.7).

The 1,2-dichloroethane mother liquors are treated with a 5% aqueous solution of NaHCO$_3$ (2×100 ml), water (2×50 ml), dried on Na$_2$SO$_4$, combined with 0,0'-dibenzoyl-L-tartaric acid (g 21.3) and then evaporated to dryness under vacuum. A stirred solution of the residue in acetonitrile (ml 600) separates after 4 hours at room temperature a crystalline precipitate (g 34, [α]$_D$=−99.6°, MeOH, c=1.2° that is recrystallized from acetonitrile (ml 600) to give g 32 of (-)-S-[(6-methyl-5-cyano-4-(3-nitrophenyl)-3-carboethoxy-1,4-dihydropyridin-2-yl)methyl]-isothiouronium 0,0'-dibenzoyl-L-tartrate (m.p. 156°-158° C., [α]$_D$=−103°, [α]$_{578}$=−108°, [α]$_{546}$=−131°, [α]$_{436}$=−355°, c=1.0, MeOH; isothiourea free base: [α]$_D$=−208°, [α]$_{578}$=−230°, [α]$_{546}$=−283°, [α]$_{436}$=−816°, c=0.5, CH$_2$Cl$_2$).

EXAMPLE 7 g 3.4 of finely powdered NaHCO$_3$ are added to a solution of g 20 of (±)S-[(6-methyl-3-carboethoxy-5-carbomethoxy-4-(2,3-dichlorophenyl)-1,4-dihydropyridin-2-yl)methyl]-isothiouronium chloride in AcOEt (ml 600) at room temperature under stirring. After 30', the organic phase is washed with water (3×100 ml), aqueous sodium bicarbonate (5%, 3×100 ml) and brine (2×50 ml) and finally is dried on Na$_2$SO$_4$. The organic phase is divided in two parts of ml 300 each, that are treated respectively with: 0,0'-dibenzoyl-L-tartaric acid (g 7.6) and 0,0'-dibenzoyl-D-tartaric acid (g 7.6). Both the solutions are left at room temperature for a night and then are filtered to give respectively g 11.3 of a levorotatory salt ([α]$_D$=−90°, c=0.5, MeOH) and g 11.1 of a dextrorotatory salt ([α]$_D$=+89°, c=0.5 MeOH). After crystallization from hot methanol (ml 220), these salts give respectively: (−)-S[(6-methyl-3-carboethoxy-5-carbonethoxy-4-(2,3-dichlorophenyl)1,4-dihydropyridin-2-yl)methyl]isothiouronium 0,0'-dibenzoyl-L-tartrate ([α]$_D$=−90°, [α]$_{578}$=−92°, [α]$_{546}$=−110°, [α]$_{436}$=−310°, c=0.5, MeOH), and (+)-S-[(6-methyl-3-carboethoxy-5-carbomethoxy-4-(2,3-dichlorophenyl)-1,4-dihydropyridin-2-yl)methyl]-isothiouronium 0,0'-dibenzoyl-D-tartrate ([α]$_D$=+89°, [α]$_{578}$=+94°, [α]$_{546}$=+114°, [α]$_{436}$=+313°, MeOH, c=0.5).

An inversion of the sign of deviation of the polarized light plane is observed when isothioureae are isolated as free bases from their isothiouronium salts. (+)-S-[(6-methyl-3-carboethoxy-5-carbomethoxy-4(2,3-dichlorophenyl)-1,4-dihydropyridin-2-yl)methyl]-isothiourea ([α]$_D$=+45°, [α]$_{578}$=+41°, [α]$_{546}$=+46°, c=0.2, MeOH) is obtained starting from (−)-isothiouronium 0,0'-dibenzoyl-L-tartrate salt while the levorotatory (−)-S-[(6-methyl-3-carboethoxy-5-carbomethoxy-4-(2,3-dichlorophenyl)-1,4-dihydropyridin-2-yl)methyl]-isothiourea ([α]$_D$=−39°, [α]$_{578}$=−40°, [α]$_{546}$=−46°, c=0.3, MeOH) is obtained from (+)-isothiouronium 0,0'-dibenzoyl-D-tartrate salt.

EXAMPLE 8

Using the procedures described in one of the examples from 1 to 7, the pure (S) and (R) enantiomers of the following isothioureae are obtained:

-S-[(6-methyl-5-cyano-4-(3-nitrophenyl)-3-carboethoxy-1,4-dihydropyridin-2-yl)methyl]-isothiourea;

-S-[(6-methyl-5-acetyl-4-phenyl-3-carboethoxy-1,4-dihydropyridin-2-yl)methyl]-isothiourea;

-S-[(6-methyl-5-carboisopropoxy-4-(3-nitrophenyl)-3-carboethoxy-1,4-dihydropyridin-2-yl)methyl]-isothiourea;

-S-[(6-methyl-3,5-dicarboethoxy-4-(2-chlorophenyl)-1,4-dihydropyridin-2-yl)methyl]-isothiourea;

-S-[(6-methyl-5-carbomethoxy-3-carboethoxy-4-(2-chlorophenyl)-1,4-dihydropyridin-2-yl)methyl]-isothiourea;

-S-[(6-methyl-5-carbomethoxy-3-carboethoxy)-4-(3-chlorophenyl)-1,4-dihydropyridin-2-yl)methyl]-isothiourea;

-S-[(6-methyl-3,5-dicarboethoxy-4-(2-trifluoromethylphenyl)-1,4-dihydropyridin-2-yl)methyl]-isothiourea;

-S-[(6-cyano-3,5-dicarbomethoxy-4-(3-trifluoromethylphenyl)-1,4-dihydropyridin-2-yl)methyl]-isothiourea;

-S-[(6-methyl-3-carboethoxy-5-allyloxycarbonyl-4-(3-nitrophenyl)-1,4-dihydropyridin-2-yl)methyl]isothiourea;

-S-[(6-methyl-3-carbomethoxy-5-(2-butenoxycarbonyl)-4-(2-chlorophenyl)-1,4-dihydropyridin-2-yl)methyl]-isothiourea;

-S-[(6-methyl-3-carboethoxy-5-tertbutoxycarbonyl-4-(3-nitrophenyl)-1,4-dihydropyridin-2-yl)methyl]-isothiourea;

-S-[(6-methyl-3-carbomethoxy-5-allyloxycarbonyl-4-(3-nitrophenyl)-1,4-dihydropyridin-2-yl)methyl]-isothiourea;

-S-[(6-methyl-3-allyloxycarbonyl-5-carbomethoxy-4-(3-nitrophenyl)-1,4-dihydropyridin-2-yl)methyl]-isothiourea;

-S-(6-methyl-3,5-diallyloxycarbonyl-4-(3-nitrophenyl)-1,4-dihydropyridin-2-yl)methyl]-isothiourea;

-S-[(-6-methyl-3-carbomethoxy-5-allyloxycarbonyl-4-(2,3-dichlorophenyl)-1,4-dihydropyridin-2-yl)methyl]-isothiourea;

-S-[(6-methyl-3-carboethoxy-5-acetyl-4-(2-thienyl)-1,4-dihydropyridin-2-yl)methyl]-isothiourea;

-S-[(6-methyl-3-carboethoxy-5-benzoyl-4-(2-thienyl)-1,4-dihydropyridin-2-yl)methyl]-isothiourea;

-S-[(6-methyl-3-carboethoxy-5-(2-phenylacetyl)-4-(pyridin-2-yl)-1,4-dihydropyridin-2-yl)methyl]-isothiourea;

-(−)-S-[(6-methyl-3-carboethoxy-5-carbomethoxy-4-(benzo-[c]-furazan-4-yl)-1,4-dihydropyridin-2-yl)methyl]-isothiourea;

-(−)-S-[(6-methyl-3-allyloxycarbonyl-5-carbomethoxy-4-(benzo-[c]-furazan-4-yl)-1,4-dihydropyridin-2-yl)methyl]-isothiourea;

-S-[(6-methyl-3-allyloxycarbonyl-5-tertbutoxycarbonyl-4-(3-nitrophenyl)-1,4-dihydropyridin-2-yl)methyl]-isothiourea;

-S-[(6-methyl-3-allyloxycarbonyl-4-tertbutoxycarbonyl-(2,3-dichlorophenyl)-1,4-dihydropyridin-2-yl)methyl]-isothiourea.

EXAMPLE 9

An aqueous solution of NaOH (20%, ml 11.5) is added to a stirred solution of (−)-S-[(6-methyl-5-cyano-4-(3-nitrophenyl)-3-carboethoxy-1,4-dihydropyridin-2-yl)methyl]-isothiouronium 0,0′-dibenzoyl-L-tartrate (g 10) and 2-bromoethylamine hydrobromide (g 6.56) in ethanol/water (50/50, ml 50), under a nitrogen atmosphere. After one hour at room temperature, the mixture is diluted with water (ml 100) and extracted with AcOEt (5×50 ml).

The combined organic phases are extracted several times with 7.5% aqueous acetic acid (4×50 ml) and then are eliminated. The combined aqueous extracts are reextracted with Et$_2$O (3×30 m) to remove neutral impurities, alkalinized by aqueous sodium bicarbonate (until pH=8.5) and finally extracted with AcOEt (4×40 ml). Said organic extracts are combined, dried and evaporated to dryness; chromatographic purification of the residue by column chromatography on SiO$_2$, (g 30, eluent CHCl$_3$/MeOH 95/5) gives g 3.4 of (−)-2-(aminoethylthio)-methyl-3-carboethoxy-5-cyano-4-(3-nitrophenyl)-6-methyl-1,4-dihydropyridine (m.p. 142°-144° C., AcOEt); $[\alpha]_D = -184°$, $[\alpha]_{578} = -196°$, $[\alpha]_{546} = -240°$ $[\alpha]_{436} = -698°$, c=1.0, MeOH).

Using in the same procedure, the (+)-S-[(6-methyl-3-carboethoxy-5-cyano-4-(3-nitrophenyl)-1,4-dihydropyridin-2-yl)methyl]-isothiouronium L-mandelate (g 4), the (+)-S-2-(aminoethyl)-thiomethyl-3-carboethoxy-5-cyano-4-(3-nitrophenyl)-6-methyl-1,4-dihydropyridine (g 2.4, m.p.=140°-144° C.; $[\alpha] = +186°$, $[\alpha]_{578} = +197°$, $[\alpha]_{546} = +240°$, $[\alpha]_{436} = +698°$, c=0.9, MeOH) are obtained.

EXAMPLE 10

A solution of (+)-S-[(6-methyl-5-carbomethoxy-3-carboethoxy-4-(3-nitrophenyl)-1,4-dihydropyridin-2-yl)methyl]-isothiouronium L-mandelate (g 8.5), N-(2-chloroethyl)-N-(2-cyanoethyl)-formamide (g 2.8) and LiOH (g 1.3) in DMF (ml 70) is stirred for 50′ at room temperature, poured into ice and saturated NaH$_2$PO$_4$ aqueous solution (ml 300) and extracted with AcOEt (3×100 ml). The combined organic phases are washed with brine (3×20 ml), dried (Na$_2$SO$_4$) and evaporated to dryness under vacuum. After purification of the residue (g 7.9) by chromatography (SiO$_2$, g 250, eluent Et$_2$O), g 5.8 of (−)-2-[2-N-formyl-N-(2-cyanoethyl)-aminoethylthio]methyl-3-carboethoxy-5-carbomethoxy-4-(3-nitrophenyl)-6-methyl-1,4-dihydropyridine are obtained as an amorphous solid ($[\alpha]_D = -17.9°$, $[\alpha]_{578} = -20°$, $[\alpha]_{546} = -25.2$; c=1.6, CH$_2$Cl$_2$).

EXAMPLE 11

Using N-(2-chloroethyl)-formamide instead of N-(2-chloroethyl)-N-(2-cyanoethyl)-formamide in the procedure of example 10, the following compounds are obtained: -(−)-2-[2-(N-formyl)aminoethylthio]-3-carboethoxy-5-carbomethoxy-4-(3-nitrophenyl)-6-methyl-1,4-dihydropyridine ($[\alpha]_D = -14°$, c=1.3, MeOH), m.p. 80°-82° C. (from Et$_2$O, white); 102°-103° C. (from AcOEt, yellow);

-(+)-2-[2-(N-formyl)aminoethylthio]-3-carboethoxy-5-carbomethoxy-4-(3-nitrophenyl)-6-methyl-1,4-dihydropyridine ($[\alpha]_D = +13.70°$, c=1.3, MeOH), m.p. 81°-83° C. (from Et$_2$O, white).

EXAMPLE 12

A mixture of (+)-S-[(6-methyl-5-nitro-4-(3-nitrophenyl)-3-carboethoxy-1,4-dihydropyridin-2-yl)methyl]-isothiouronium D-mandelate (4.0 g), 2-bromoethylamine hydrobromide (g 10.7), hexadecyl-tributylphosphonium bromide (g 1.0), benzene (ml 40) and NaOH (20%, ml 11.4) is vigorously stirred for 10′, and then diluted with a mixture of water (ml 200) and AcOEt (ml 100). After separation of the phases, the aqueous phase is reextracted with AcOEt (2×30 ml) and eliminated. The organic phases are combined, washed with NaHCO$_3$ (saturated solution 2×50 ml), dried (Na$_2$SO$_4$) and then evaporated to dryness in the presence of SiO$_2$ (g 15).

The residue is eluted through a chromatographic column (SiO$_2$ g 60), using MeOH/CHCl$_3$ 10/90 as eluent.

The eluted fractions, containing the desired amine, are combined and after addition of fumaric acid (g 0.6) are evaporated to dryness under vacuum.

By trituration of the residue with Et$_2$O, g 2.2 of (+)-2-(2-aminoethylthio)-methyl-5-nitro-4-(3-nitrophenyl)-6-methyl-3-carboethoxy-1,4-dihydropyridine hemifumarate ($[\alpha]_D = +56°$, c=2.0 DMF) are obtained.

Using in the same procedure the levorotatory isothiouronium salt the:

(−)-2-(2-aminoethylthio)methyl-5-nitro-4-(3-nitrophenyl)-3-carboethoxy-6-methyl-1,4-dihydropyridine hemifumarate ($[\alpha]_D = 54°$, c=2.0, DMF) is also prepared.

EXAMPLE 13

A solution of 1-formylimidazole (prepared reacting carbonyldiimidazole, g 3.3, with formic acid, ml 0.80 at 0° C., in THF (ml 30)) is added dropwise to a solution in dry THF (ml 15) cooled at 0° C. of (−)-2-[(1,4,5,6-tetrahydropyrimidin-2-yl)thio]methyl]-3,5-dicarboethoxy-4-(3-nitrophenyl)-6-methyl-1,4-dihydropyridine (g 5.1; free base, isolated from the mandelate salt by treatment with AcOEt/aqueous Na$_2$CO$_3$).

The mixture is stirred for 1 hour at room temperature, diluted with water (150 ml) and extracted with diethyl ether (3×30 ml). The combined organic phases are dried (Na$_2$SO$_4$), evaporated under vacuum and the residue is triturated with cold ethanol to give g 4.5 of (−)-2-[(1-formyl-1,4,5,6-tetrahydropyrimidin-2-yl)thio]methyl-3,5-dicarboethoxy-4-(3-nitrophenyl)-6-methyl-1,4-dihydropyridine.

$^1$HNMR (CDCl$_3$) δ: 1.0–1.2 (6H) 1.8–2.3 (5H) 4.4–4.8 (6H) 5.1 (1H) 6.9 (1H) 7.1 8.2 (4H) 9.2 (1H).

EXAMPLE 14

A mixture of (+)-S-[(5-carbomethoxy-3-carboethoxy-4-(3-nitrophenyl)-6-methyl-1,4-dihydropyridin-2-yl)-methyl]-isothiouronium chloride (mg 500), t-butyl chloroacetate (mg 230), NaOH (35%, ml 2), benzyltriethylammonium bromide (BTEAB, mg 73) and 1,2-dichloroethane (ml 5) is stirred at room temperature for two hours, and diluted with water (ml 5). The organic phase is separated, washed with water (4×3 ml), dried (Na$_2$SO$_4$) and evaporated under vacuum to crystallize from diethyleter g 0.48 of (+)-2-(tert-butoxycarbonylmethylthio)methyl-3-carboethoxy-5-carbomethoxy-4-(3-nitrophenyl)-6-methyl-1,4-dihydropyridine.

$^1$HNMR (CDCl$_3$) δ: 0.91.2 (12H) 2.1 (3H) 3.43.8 (4H) 4.34.8 (6H) 5.1 (1H) 7.08.2 (5H).

EXAMPLE 15

A mixture of (−)-S-[(5-cyano-3-carboethoxy-4-(3-nitrophenyl)-6-methyl-1,4-dihydropyridin-2-yl)methyl-]isothiourea (mg 500), 3-chloromethylpyridinium hydrochloride (mg 190), benzylthriethylammonium chloride (BTEAC mg 80), KOH (4M, ml 2) and benzene (ml 5) is stirred at room temperature for 15 minutes to separate a precipitate that is filtered and triturated with diethyl ether to give mg 450 of (−)-2-(3-pyridinylmethylthio)methyl-5-cyano-3-carboethoxy-4-(3-nitrophenyl)-6-methyl-1,4-dihydropyridine.

$^1$H NMR (CDCl$_3$) δ: 1.9–1.1 (3H) 2.3 (3H) 4.3–4.9 (6H) 5.1 (1H) 6.8 (1H) 7.2–8.2 (4H).

EXAMPLE 16

A mixture of (+)-S-[(5-carbomethoxy-3-carboethoxy-4-(3-nitrophenyl)-6-methyl-1,4-dihydropyridin-2-yl)methyl]-isothiourea (mg 500), 2,4-difluorobenzenediazonium tetrafluoroborate (mg 242), K$_2$CO$_3$ (mg 440) and BTEAC (mg 73) in benzene (ml 5) is stirred at room temperature for 6 hours. mg 30 of (+)-2-(2,4-difluorophenylthio)-methyl-3-carboethoxy-5-carbomethoxy-4-(m-nitrophenyl)-6-methyl-1,4-dihydropyridine (as an amorphous solid) are obtained after the usual work-up and chromatographic purification on SiO$_2$ (g 15, eluted in order with hexane/diisopropyl ether 50/50 and with hexane/ethyl acetate 80/20).

$^1$NMR (δ CDCl$_3$) = 8.05–6.65 (8H,m) 5.05 (1H,s) 4.41 (2H,sb), 4.10 (2H,q) 3.60 (3H,s) 2.18 (3H,s) 1.14 (3H,t).

EXAMPLE 17

A mixture of (−)-2-[(1,4,5,6-tetrahydropyrimidin-2-yl)thio]methyl-3-carboethoxy-5-carbomethoxy-4-(m-nitrophenyl)-6-methyl-1,4-dihydropyridine (g 2), hexadecyltributyl phosphonium bromide (mg 180), 2-bromoethylaminehydrobromide (mg 900), NaOH (35%, ml 8) and benzene is stirred for 40 minutes at room temperature. After the usual work-up, an oily residue is obtained that is dissolved in ethyl acetate and treated with fumaric acid to give 1.9 g of (−)-2-(aminoethylthio)methyl-3-carboethoxy-5-carbomethoxy-4-(3-nitrophenyl)-6-methyl-1,4-dihydropyridine fumarate, m.p. 104°–110° C. [α]$_D$ = −11 (C=4 in MeOH).

EXAMPLE 18

Using in the procedures described in examples 13–17, a solvent selected from the group of benzene, toluene, 1,2-dichloroethane, methylene chloride, ethyl acetate, a base selected from the group of K$_2$CO$_3$, Na$_2$CO$_3$, KOH and NaOH and a "phase transfer" catalyst selected from the group of tetrabutylammonium bromide, benzyltriethylammonium chloride, benzyltriethylammonium bromide, dodecyltrimethylammonium bromide, hexadecyltrimethylammonium chloride and hexadecyltrimethylammonium bromide, by reaction of a suitable electrophilic reagent (selected in the group of alkyl halide and sulphate or sulphonate, diazonium salts and of a Michael acceptor, such as α- and β- unsaturated esters, ketones and/or nitriles) with a racemic salt of: S-(1,4-dihydropyridin-2-yl-methyl)-isothiouronium as those described in preparations 1–5, and/or with a diastereoisomerically pure isothiouronium salt and/or with an enantiomerically pure S-(1,4-dihydropyridin-2-ylmethyl)-isothiourea of examples 2–8, the following 6-methyl-1,4-dihydropyridines are obtained as pure enantiomers and/or racemates (±):

-2-(2-cyanoethylthiomethyl)-5-cyano-3-carboethoxy-4-(3-nitrophenyl), (+) m.p. 136°–137° C.;

-2-(2-cyanoethylthiomethyl)-5-carboisopropoxy-3-carboethoxy-4-(3-nitrophenyl), (+) m.p. 95°–98° C.;

-2-(2-cyanoethylthiomethyl)-3,5-dicarboethoxy-4-(2-chlorophenyl);

-2-(2-cyanoethylthiomethyl)-5-carbomethoxy-3-carboethoxy-4-(2-chlorophenyl);

-2-(2-cyanoethylthiomethyl)-5-carbomethoxy-3-carboethoxy-4-(3-chlorophenyl);

-2-(2-cyanoethylthiomethyl)-3,5-dicarboethoxy-4-(2-trifluoromethylphenyl);

-2-(2-cyanoethylthiomethyl)-5-carbomethoxy-3-carboethoxy-4-(2-trifluoromethylphenyl);

-2-(2-cyanoethylthiomethyl)-5-carbomethoxy-3-carboethoxy-4-(3-trifluoromethylphenyl);

-2-(2-cyanoethylthiomethyl)-5-carbomethoxy-3-carboethoxy-4-(phenyl);

-2-(2-cyanoethylthiomethyl)-5-carbomethoxy-3-carboethoxy-4-(4-nitrophenyl);

-2-(2-cyanoethylthiomethyl)-5-carbomethoxy-4-(2-nitrophenyl);

-2-(2-aminoethylthio)methyl-5-carbomethoxy-3-carboethoxy-4-(3-methoxyphenyl), (+) m.p. 124°–130° C. (fumarate);

-2-(2-aminoethylthio)-methyl-5-carbomethoxy-3-carboethoxy-4-(3-cyanophenyl), (+) m.p. 172°–174° C. (fumarate), 99°–100° C. (base);

-2-(2-aminoethylthio)-methyl-5-carbomethoxy-3-carboethoxy-4-(2,3-dichlorophenyl), (+) m.p. 128°–130° C. (fumarate);

-2-(2-aminoethylthio)-methyl-5-carbomethoxy-3-carboethoxy-4-(4-chlorophenyl), (+) m.p. 89°–91° C. (base);

-2-(2-aminoethylthio)methyl-5-nitro-3-carboethoxy-4-(3-nitrophenyl), (+) m.p. 182°–185° C. (fumarate);

-2-(2-N,N-dimethylaminoethylthio)-methyl-5-carbomethoxy-3-carboethoxy-4-(3-nitrophenyl), (+) m.p. 191°–194° C. (hydrochloride);

-2-(2-N-methylaminoethylthio)-methyl-5-carbomethoxy-3-carboethoxy-4-(3-nitrophenyl), (+) m.p. 205°–207° C. (fumarate);

-2-(2-N-butylaminoethylthio)-methyl-3,5-dicarboethoxy-4-(3-nitrophenyl), (+) m.p. 129°–131° C. (hydrochloride);

-2-(2-N-acetylaminoethylthio)-methyl-5-carboethoxy-3-carbomethoxy-4-(3-nitrophenyl), (+) m.p. 115°–116° C.;

-2-(2-N-formylaminoethylthio)-methyl-5-carboethoxy-3-carbomethoxy-4-(3-nitrophenyl), (+) m.p. 111°–112° C.;

-2-[2-N-(2-cyanoethyl)aminoethylthio]methyl-3,5-dicarboethoxy-4-(3-nitrophenyl), (+) m.p. 105°-107° C. (fumarate);

-2-[2-N-formyl-N-(2-cyanoethyl)aminoethylthio]methyl-5-carbomethoxy-3-carboethoxy-4-(3-nitrophenyl), (+) m.p. 114°-115° C.;

-2-(2,3-dihydroxyethylthio)methyl-3,5-dicarboethoxy-4-(3-nitrophenyl) (+) m.p. 98°-102° C.;

-2-(2,3-dihydroxyethylthio)methyl-5-carbomethoxy-3-carboethoxy-4-(2-chlorophenyl);

-2-(2-hydroxyethylthio)methyl-3,5-dicarboethoxy-4-(3-nitrophenyl), (±) m.p. 119°-120° C.; (−) m.p. 127°-128° C. $[\alpha]_D = -8.1$; (+) m.p. 128°-129° C. $[\alpha]_D = +9°$ C. (c=1 MeOH);

-2-allylthiomethyl-5-carbomethoxy-3-carboethoxy-4-(3-nitrophenyl), (+) m.p. 74°-77° C.;

-2-(2-propargylthiomethyl-5-carbomethoxy-3-carboethoxy-4-(3-nitrophenyl), (+) m.p. 110°-112° C.;

-2-ethylthiomethyl-3,5-dicarboethoxy-4-(3-nitrophenyl), (+) m.p. 120°-121° C.;

-2-benzylthiomethyl-3,5-dicarboethoxy-4-(3-nitrophenyl), (+) m.p. 91°-93° C.;

-2-phenylethylthiomethyl-3,5-dicarboethoxy-4-(3-nitrophenyl), (+) m.p. 73°-75° C.;

-2-(2-nitrophenylthio)-methyl-3,5-dicarboethoxy-4-(3-nitrophenyl), (+) m.p. 135°-136° C.;

-2-furfurylthiomethyl-3,5-dicarboethoxy-4-(3-nitrophenyl), (+) m.p. 73°-75° C.;

-2-(3-pyridinylmethyl)-thiomethyl-3,5-dicarboethoxy-4-(3-chlorophenyl);

-2-furfurylthiomethyl-3,5-dicarboethoxy-4-(3-chlorophenyl);

-2-[2-(2-phenyl-2-oxoethyl)-thio]-methyl-3-carboethoxy-5-carbomethoxy-4-(3-nitrophenyl), (+) m.p. 152°-154° C.;

-2-[(oxyran-2-yl)methylthio]-methyl-3,5-dicarboethoxy-4-(3-nitrophenyl), (+) m.p. 107°-109° C.;

-2-](oxyran-2-yl)-methylthio]-methyl-3-carboethoxy-5-carbomethoxy-4-(3-chlorophenyl) (+) m.p. 80°-84° C.;

-2-[4-(N-phtalimido)-butylthio]-methyl-3-carboethoxy-5-carbomethoxy-4-(3-nitrophenyl), (+) m.p. 125°-127° C.;

-2-(2-aminoethylthio)-methyl-5-[2-(N-benzyl-N-methyl)-amino]-ethoxycarbonyl-3-ethoxycarbonyl-4-(3-nitrophenyl), (+) m.p. 135°-136° C. (. 2 HCl . H₂O);

-2-[2-(N-N-butylaminoethylthio)-methyl-3-carboethoxy-5-nitro-4-(3-nitrophenyl), (+) m.p. 198°-200° C. (fumarate);

-2-(2-aminoethylthio)-methyl-3-carboethoxy-5-nitro-4-(3-trifluoromethylphenyl), (+) m.p. 152°-155° C. (fumarate);

-2-(2-aminoethylthio)-methyl-3-carboethoxy-5-cyano-4-(3-nitrophenyl), (+) m.p. 181°-183° C. (fumarate);

-2-(2-aminoethylthio)-methyl-5-tert-butoxycarbonyl-3-ethoxycarbonyl-4-(3-nitrophenyl);

-(+)-2-(2-N-formylaminoethylthio)-methyl-3-carboethoxy-5-cyano-4-(3-nitrophenyl), m.p. 143°-146° C.; $[\alpha]_D = +164.5°$, (c=1.4 MeOH);

-(−)-2-(2-N-formylaminoethylthio)-methyl-3-carboethoxy-5-cyano-4-(m-nitrophenyl), m.p. 143°-145° C.; $[\alpha]_D - 165°$, c=1.5, MeOH);

-(+)-2-(2-N-formyl-N-2-cyanoethylaminoethylthio)-methyl-3-carboethoxy-5-cyano-4-(3-nitrophenyl), $[\alpha]_D = +113°$, c=1.7, MeOH);

-(−)-2-(2-N-formyl-N-2-cyanoethylaminoethylthio)-methyl-3-carboethoxy-5-cyano-4-(3-nitrophenyl), $[\alpha]_D = -111°$, c=1.7, MeOH);

-(+)-2-(aminoethylthio)-methyl-3-carboethoxy-5-carbomethoxy-4-(3-nitrophenyl) fumarate ($[\alpha]_D = +13°$, c=4, MeOH);

-(−)-2-(aminoethylthio)-methyl-3-carboethoxy-5-carbomethoxy-4-(3-nitrophenyl) fumarate $[\alpha]_D = -11°$, c=4, MeOH);

-(+)-2-(2-N-formylaminoethylthio)-3-carboethoxy-5-nitro-4-(3-nitrophenyl), ($[\alpha]_D = +6.2°$, c=2.0 DMF);

-(−)-2-(2-N-formylaminoethylthio)-3-carboethoxy-5-nitro-4-(3-nitrophenyl), ($[\alpha]_D = -5.7°$, c=2.0 DMF);

-(+)-2-(cyanoethylthio)-methyl-5-carbomethoxy-3-carboethoxy-4-(2-chlorophenyl);

-(−)-2-(cyanoethylthio)-methyl-5-carbomethoxy-3-carboethoxy-4-(2-chlorophenyl);

-(+)-2-(methylthio)-methyl-5-nitro-3-carboethoxy-4-(3-nitrophenyl);

-(−)-2-(methylthio)-methyl-5-nitro-3-carboethoxy-4-(3-nitrophenyl);

-(+)-2-(methylthio)-methyl-5-nitro-3-carbomethoxy-4-(2-trifluoromethylphenyl);

-(−)-2-(methylthio)-methyl-5-nitro-3-carbomethoxy-4-(2-trifluoromethylphenyl);

-(+)-2-(methylthio)-methyl-5-cyano-3-carbomethoxy-4-(2-trifluoromethylphenyl);

-(−)-2-(methylthio)-methyl-5-cyano-3-carbomethoxy-4-(2-trifluoromethylphenyl);

-(+)-2-(methylthio)-methyl-5-carbomethoxy-3-carboethoxy-4(3-nitrophenyl) m.p. 87°-88° C. $[\alpha]_D = +24.8°$, $[\alpha]_{578} = +27.1°$ $[\alpha]_{546} = +36.4$, c=2.1 EtOH;

-(−)-2-(methylthio)-methyl-5-carbomethoxy-3-carboethoxy-4-(3-nitrophenyl) m.p. 88°-89° C. $[\alpha]_D = -24.5°$, $[\alpha]_{578} = -26.7°$ $[\alpha]_{546} = -36.2$, c=2.1 EtOH;

-(+)-2-(benzylthio)-methyl-5-nitro-3-carboethoxy-4-(1,4-benzodioxane-5-yl);

-(−)-2-(benzylthio)-methyl-5-nitro-3-carboethoxy-4-(1,4-benzodioxan-5-yl);

-(+)-2-(benzylthio)-methyl-5-cyano-3-carboethoxy-4-(1,4-benzodioxan-5-yl);

-(−)-2-(benzylthio)-methyl-5-cyano-3-carboethoxy-4-(1,4-benzodioxan-5-yl);

-(+)-2-(benzylthio)-methyl-3,5-dicarboethoxy-4-(benzodioxan-5-yl);

-(−)-2-(benzylthio)-methyl-3,5-dicarboethoxy-4-(benzdioxan-5-yl);

-(+)-2-(3-pyridinylmethyl)-thiomethyl-3,5-dicarbomethoxy-4-(benzodioxan-6-yl);

-(−)-2-(3-pyridinylmethyl)thiomethyl-3,5-dicarbomethoxy-4-(benzodioxan-6-yl);

-(+)-2-(3-pyridinylmethyl)-thiomethyl-3,5-dicarbomethoxy-4-(benzofurazan-4-yl);

-(+)-2-(3-pyridinylmethyl)-thiomethyl-5-cyano-3-carbomethoxy-4-(benzofurazan-4-yl);

-(−)-2-(3-pyridinylmethyl)-thiomethyl-5-cyano-3-carbomethoxy-4-(benzofurazan-4-yl);

-(+)-2-(3-pyridinylmethyl)-thiomethyl-5-nitro-3-carboterbutoxy-4-(benzofurazan-4-yl);

-(−)-2-(3-pyridinylmethyl)-thiomethyl-5-nitro-3-carboterbutoxy-4-(benzofurazan-4-yl);

-(+)-2-(tertbutoxycarbonylthio)-methyl-5-nitro-3-carboethoxy-4-(2,3-dichlorophenyl);

-(−)-2-(tertbutoxycarbonylthio)-methyl-5-nitro-3-carboethoxy-4-(2,3-dichlorophenyl);

-(+)-2-(tertbutoxycarbonylthio)-methyl-5-cyano-3-carboethoxy-4-(2,3-dichlorophenyl);

-(−)-2-(tertbutoxycarbonylthio)-methyl-5-cyano-3-carboethoxy-4-(2,3-dichlorophenyl);

-(−)-2-(tertbutoxycarbonylthio)-methyl-5-carbomethoxy-3-carboethoxy-4-(2,3-dichlorophenyl);

-(+)-2-(aminoethylthio)-methyl-3-carboethoxy-5-carbomethoxy-4-(3-nitrophenyl) fumarate (m.p. 105°–112° C. $[\alpha]_D = +3.6°$, MeOH, c=9.4);

-(−)-2-(aminoethylthio)-methyl-3-carboethoxy-5-carbomethoxy-4-(3-nitrophenyl) fumarate (m.p. 104°–115° C. $[\alpha]_D = -3.4°$, MeOH, c=9.7);

-(+)-2-(2-aminoethylthio)-methyl-3-carboethoxy-5-carbomethoxy-4-(3-chlorophenyl);

-(−)-2-(2-aminoethylthio)-methyl-3-carboethoxy-5-carbomethoxy-4-(3-chlorophenyl);

-(+)-2-(2-aminoethylthio)-methyl-3-carboethoxy-5-allyloxycarbonyl-4-(3-chlorophenyl);

-(+)-2-(2-aminoethylthio)-methyl-3-carboethoxy-5-allyloxycarbonyl-4-(3-chlorophenyl);

-(+)-2-(2-aminoethylthio)-methyl-3-carboethoxy-5-terbutoxycarbonyl-4-(3-nitrophenyl);

-(−)-2-(2-aminoethylthio)-methyl-3-carboethoxy-5-terbutoxycarbonyl-4-)3-nitrophenyl);

-(+)-2-(2-N-formylaminoethylthio)-methyl-3-tert-butoxycarbonyl-5-cyano-4-(3-nitrophenyl);

-(−)-2-(2-N-formylaminoethylthio)-methyl-3-tert-butoxycarbonyl-5-cyano-4-(3-nitrophenyl);

-(+)-2-(2-N-formylaminoethylthio)-methyl-3-tert-butoxycarbonyl-5-nitro-4-(2-trifluoromethylphenyl);

-(−)-2-(2-N-formylaminoethylthio)-methyl-3-tert-butoxycarbonyl-5-nitro-4-(2-trifluoromethylphenyl);

-(+)-2-(2-N-acetylaminoethylthio)-methyl-3-carboethoxy-5-carbomethoxy-4-(3-nitrophenyl) (m.p. 127°–131° C., $[\alpha]_D = +15.3°$, MeOH, c=3.3);

-(−)-2-(2-N-acetylaminoethylthio)-methyl-3-carboethoxy-5-carbomethoxy-4-(3-nitrophenyl) (m.p. 125°–128° C., $[\alpha]_D = -15.0°$, MeOH, c=3.7);

-(+)-2-(2-aminoethylthiomethyl-3-carboethoxy-5-carbomethoxy-4-(3-pyridinyl);

-(−)-2-(2-aminoethylthiomethyl-3-carboethoxy-5-carbomethoxy-4-(3-pyridinyl);

-(+)-2-(2-N-formylaminoethylthio)-methyl-3-carboethoxy-5-nitro-4-(3-pyridinyl);

-(−)-2-(2-N-formylaminoethylthio)-methyl-3-carboethoxy-5-nitro-4-(3-pyridinyl);

-(+)-2-(2-N-formylaminoethylthio)-methyl-3-carboethoxy-5-cyano-4-(2-furanyl);

-(−)-2-(2-N-formylaminoethylthio)-methyl-3-carboethoxy-5-cyano-4-(2-furanyl);

-(+)-2-(benzylthio)-methyl-3-carboethoxy-5-cyano-4-(2-phenyl);

-(−)-2-(benzylthio)-methyl-3-carboethoxy-5-cyano-4-(2-phenyl);

-(+)-2-(benzylthio)-methyl-3,5-dicarboethoxy-4-(3-nitrophenyl) ($[\alpha]_D = +25.5°$, $[\alpha]_{578} = +26.4°$, $[\alpha]_{546} = +29.8°$, c=2.1 CH$_2$Cl$_2$);

-(−)-2-(benzylthio)-methyl-3,5-dicarboethoxy-4-(3-nitrophenyl) ($[\alpha]_D = -26.3°$, $[\alpha]]_{578} = -27.2°$, $[\alpha]_{546} = -30.4°$, c=2.8 CH$_2$Cl$_2$);

and the following disubstituted 1,4-dihydropyridines:

-(+)-2-(benzylthio)-methyl-3-carboethoxy-5-carbomethoxy-4-(3-nitrophenyl)-6-fluoromethyl-1,4-dihydropyridine;

-(−)-2-(benzylthio)-methyl-3,5-dicarboethoxy-4-(3-nitrophenyl)-6-fluoromethyl-1,4-dihydropyridine;

-(+)-2-(2-aminoethylthio)-methyl-3-carboethoxy-5-carbomethoxy-4-(3-nitrophenyl)-6-fluoromethyl-1,4-dihydropyridine;

-(−)-2-(2-aminoethylthio)-methyl-3-carboethoxy-5-carbomethoxy-4-(3-nitrophenyl)-6-fluoromethyl-1,4-dihydropyridine;

-(+)-2-(2-N-formylaminoethylthio)-methyl-3-carboethoxy-5-carbomethoxy-4-(3-nitrophenyl)-6-fluoromethyl-1,4-dihydropyridine;

-(−)-2-(2-N-formylaminoethylthio)-methyl-3-carboethoxy-5-carbomethoxy-4-(3-nitrophenyl)-6-fluoromethyl-1,4-dihydropyridine;

-(+)-2-(2-aminoethylthio)-methyl-3,5-dicarboethoxy-4-(3-chlorophenyl)-6-formyl-1,4-dihydropyridine;

-(−)-2-(2-aminoethylthio)-methyl-3,5-dicarboethoxy-4-(3-chlorophenyl)-6-formyl-1,4-dihydropyridine;

-(+)-2-(2-N-formylaminoethylthio)-methyl-3-carboethoxy-5-nitro-4-(3-pyridinyl)-6-diethoxymethyl-1,4-dihydropyridine;

-(−)-2-(2-N-formylaminoethylthio)-methyl-3-carboethoxy-5-nitro-4-(3-pyridinyl)-6-diethoxymethyl-1,4-dihydropyridine;

-(+)-2-(benzylthio)-methyl-3-carboethoxy-5-(2-methoxyethoxy)-4-(3-thienyl)-6-cyano-1,4-dihydropyridine;

-(−)-2-(benzylthio)-methyl-3-carboethoxy-5-(2-methoxyethoxy)-4-(3-thienyl)-6-cyano-1,4-dihydropyridine;

-(+)-2-(2-aminoethylthio)-methyl-3,5-dicarboethoxy-4-(3-chlorophenyl)-6-cyano-1,4-dihydropyridine;

-(−)-2-(2-aminoethylthio)-methyl-3,5-dicarboethoxy-4-(3-chlorophenyl)-6-cyano-1,4-dihydropyridine;

-2-(2-aminoethylthio)-methyl-3-carboethoxy-5-carbomethoxy-4-phenyl-6-methyl-1,4-dihydropyridine.

EXAMPLE 19

Under inert gas atmosphere, a stirred suspension of (+)-2-(2-chloroethyl)-3-carboethoxy-5-carbomethoxy-4-(2,3-dichlorophenyl)-6-methyl-1,4-dihydropyridine (g 6.4), thiourea (g 1.5) in N-methylpyrrolidone (ml 25) is heated at 95°–105° C. to give a complete solution. 20 minutes after, the mixture is cooled to 40°–50° C., diluted with AcOEt (40 ml) and filtered to obtain g 6.2 of (+)-S-[(6-methyl-3-carboethoxy-5-carbomethoxy-4-(2,3-dichlorophenyl)-1,4-dihydropyridin-2-yl)ethyl]-isothiouronium chloride.

In a period of 15 minutes, finely powdered NaHCO$_3$ is added to a vigorously stirred suspension of the isothiouronium salt, in AcOEt/water (60 ml/20 ml); the mixture is stirred to obtain a complete dissolution of the reagents. The aqueous phase is eliminated; after the usual work-up from the organic phase g 5.6 of (+)-S-[(6-methyl-3-carboethoxy-5-carbomethoxy-4-(2,3-dichlorophenyl)-1,4-dihydropyridin-2-yl)ethyl]-isothiourea are obtained by crystallization from Et$_2$O/MeOH.

A solution of the thiourea in acetonitrile (50 ml) is treated with (L)-mandelic acid (g 2.05) to obtain 2.3 g of (+)-S-[(6-methyl-3-carboethoxy-5-carbomethoxy-4-(2,3-dichlorophenyl)ethyl]-isothiouronium L-mandelate.

Under inert gas atmosphere, a stirred solution of this salt in DMF (10 ml) is treated with KHCO$_3$ (g 0.8) and after 10 minutes, with a Ni Raney suspension (g 10 of an aqueous suspension) in DMF (10 ml). After an hour at room temperature, the mixture is filtered on "celite", the filtrate is concentrated under vacuum to a small volume (5 ml), diluted with water (50 ml) and extracted with AcOEt (4×10 ml). After the usual work-up, by evaporation of the solvent and crystallization from Et₂O, g 1.1 of (+)-2-ethyl-6-methyl-3-carboethoxy-5-carbomethoxy-4-(2,3-dichlorophenyl)-1,4-dihydropyridine are obtained. Using in the same procedure the enantiomer (D)-mandelic acid, (+)-2-ethyl-6-methyl-3-carboethoxy-5-carbomethoxy-4-(2,3-dichlorophenyl)-1,4-dihydropyridine is obtained.

EXAMPLE 20

Under inert gas atmosphere, a solution of (−)-2-[(1,4,5,6-tetrahydropyrimidin-2-yl)thio]methyl-3-carboethoxy-5-carbomethoxy-4-(3-trifluoromethylphenyl)-6-methyl -1,4-dihydropyridine (g 6.5) in EtOH (ml 20) and KHCO₃ (g 0.4) is added dropwise to a stirred Ni-Raney suspension (g 13) in EtOH. After 30 minutes, the solution is filtered, evaporated to dryness under vacuum and the residue is partitioned between AcOEt (ml 30) and water.

1.9 g of (−)-2,6-dimethyl-3-carboethoxy-5-carbomethoxy-4-(3-trifluoromethylphenyl)-1,4-dihydropyridine, m.p. 134°-135° C. are obtained from the organic phase after the usual work-up and crystallization from Et₂O.

EXAMPLE 21

Desulfuration, with Ni-Raney (g 10) suspended in DMF (ml 10), of a solution of KHCO₃ (g 0.67) and of 3 g of (−)-S-[6-methyl-3-carboethoxy-5-carbomethoxy-4-(2,3-dichlorophenyl)-1,4-dihydropyridin-2-yl)methyl]-isothiouronium L-0,0'-dibenzoyltartrate in DMF (ml 10) at room temperature for an hour produces g 1.09 of (−)-2,6-dimethyl-3-carboethoxy-5-carbomethoxy-4-(2,3-dichlorophenyl)-1,4-dihydropyridine (m.p. 140°-141° C. [α]$_D$=−4.4°, c=4.1, CH₂Cl₂).

EXAMPLE 22

Under nitrogen atmosphere and stirring, a MeOH solution (15 ml) of g 0.85 of (+)2-ethylthiomethyl-3-carboethoxy-5-carbomethoxy-4-(3-chlorophenyl)-6-methyl-1,4-dihydropyridine, cooled at 30° C. is treated with NaH₂PO₄ (g 1.45) and with Na/Hg amalgam (2.64 g) (10% in Na). After 15 minutes the solution is filtered and evaporated to a small volume under vacuum. The residue is partitioned between water (ml 20) and AcOEt (3×30 ml), the organic phases are collected to give after the usual work-up 0.56 g of (+)-2,6-dimethyl-4-(3-chlorophenyl)-3-carboethoxy-5-carbomethoxy-1,4-dihydropyridine [α]$_D$=+5.5°; c=4.1 CH₂Cl₂.

EXAMPLE 23

Under nitrogen atmosphere, a stirred solution of (+)-2-ethylthiomethyl-3-carboethoxy-5-allyloxycarbonyl-4-(2,3-dichlorophenyl)-methyl-1,4-dihydropyridine (g 1.1), ammonium formate (g 0.4), triphenylphosphine (g 0.02) in dioxane (15 ml) is treated with 10% Pd on C (0.03 g) and heated at the reflux temperature for an hour. The mixture is filtered, concentrated to a small volume, diluted with ice (10 g) and NaOH 1N (30 ml) and finally extracted with AcOEt (2×8 ml). The organic extracts are eliminated while the aqueous phase is acidified with H₂SO₄ 2N to pH 12. A precipitate (g 0.78) of (+)-2-ethylthiomethyl-3-carboethoxy-5-carboxy-4-(2,3-dichlorophenyl)-6-methyl-1,4-dihydropyridine is collected by filtration and dried under vacuum.

EXAMPLE 24

Under an inert gas atmosphere, a stirred aqueous suspension of Ni-Raney (3 g) is added to a solution of g 1.5 of (−)-S-[6-methyl-3-carbomethoxy-5-nitro-4-(2-trifluoromethylphenyl)-1,4-dihydropyridin-2-yl)methyl-]isothiourea in DMF (12 ml). After 20 minutes at room temperature, the mixture is filtered, diluted with water, acidified with H₂SO₄ 2N to pH 2.3 and extracted with AcOEt (3×20 ml). After usual working of the organic phase, g 1.04 of (−)-2,6-dimethyl-3-carbomethoxy-5-nitro-4-(2-trifluoromethylphenyl)-1,4-dihydropyridine m.p. 131°-133° C., [α]$_D$=−22.1, [α]$_{546}$=−32.7 (c=1.88 dioxane) are obtained.

EXAMPLE 25

Using in the procedure of example 24, the (−)-S-[6-methyl-3-carbomethoxy-5-nitro-4-(2-trifluoromethylphenyl)-1,4-dihydropyridin-2-yl)methyl]-isothiouronium, 0,0-dibenzoyl-L-tartrate (m.p. 163°-164° C.; [α]$_D$=−72, c=2.03 MeOH) and the following isothioureas: (−)-S-[6-methyl-3-carbomethoxy-5-nitro-4-(3-nitrophenyl)-1,4-dihydropyridin-2-yl)methyl]-isothiourea and (−)-S-[6-methyl-3-carboethoxy-5-carbomethoxy-4-(3-nitrophenyl)-1,4-dihydropyridin-2-yl)methyl]-isothiourea the followings: (+)2,6-dimethyl-3-carbomethoxy-5-nitro-4-(2-trifluoromethylphenyl)-1,4-dihydropyridine m.p. 65°-70° C., [α]$_D$=+20.1 (c=1.91 dioxane); 2,6-dimethyl-3-carbomethoxy-5-nitro-4-(3-nitrophenyl)-1,4-dihydropyridine and 2,6-dimethyl-3-carboethoxy-5-carbomethoxy-4-(3-nitrophenyl)-1,4-dihydropyridine, m.p. 158°-159° C.; [α]$_D$=+16.3°, c=2,1 EtOH, are obtained with a 40-45% yield.

EXAMPLE 26

Under nitrogen atmosphere, a stirred solution of (+)-2-methylthiomethyl-6-methyl-5-carbomethoxy-3-carboethoxy-4-(3-nitrophenyl)-1,4-dihydropyridine (g 1.5) in anhydrous 1,2-dimethoxyethane is treated with g 1.6 of trimethyloxonium tetrafluoborate at room temperature for 30 minutes to separate a crystalline precipitate of (+)-S-dimethyl-[6-methyl-5-carbomethoxy-3-carboethoxy-4-(3-nitrophenyl)-1,4-dihydropyridin-2-yl]-methylsulphoxonium tetrafluoborate (g 1.8, m.p. 165°-166° C.).

EXAMPLE 27

Using in the procedure of example 26 2-alkylthiomethyl and/or 2-benzylthiomethyl-1,4-dihyropyridines, the following sulphonium salts are also obtained:
-(−)-S-methyl,ethyl-[6-methyl-5-cyano-3-carboethoxy-4(3-nitrophenyl)-1,4-dihydropyridin-2-yl]-methylsulphonium tetrafluoborate,
-(+)-S-methyl,benzyl-[6-methyl-5-nitro-3-carboethoxy-4-(1,4-benzodioxan-5-yl)-1,4-dihydropyridin-2-yl]-methylsulphonium tetrafluoborate,
-(−)-S-[N-2-formylamino]ethyl,methyl-[6-methyl-5-carbomethoxy-3-carboethoxy-4-(3-nitrophenyl)-1,4-dihydropyridin-2-yl]-methylsulphonium tetrafluoborate.

EXAMPLE 28

A solution of sulphonium salts of examples 26 and 27 (for instance a stirred solution of (+)-S-methylbenzyl-[6-methyl-5-nitro-3-carboethoxy-4-(1,4-benzodioxan-5-yl)-1,4-dihydropyridin-2-yl]-methylsulphonium tetrafluoborate (g 1.8) in DMSO (ml 16), cooled at 5°-10° C., is treated with 0.15 g of sodium borohydride added at small portions. The solution at room temperature is stirred for further 15 minutes, diluted with water (ml 100) and extracted with AcOEt (3×30 ml). From the organic phases, after the usual work-up and crystallization from ethyl ether, g 1.1 of (+)-2,6-dimethyl-5-nitro-3-carboethoxy-4-(1,4-benzodioxan-5-yl)-1,4-dihydropyridine are obtained. In the same way, the following compounds are prepared.
(+)-2,6-dimethyl-5-carbomethoxy-3-carboethoxy-4-(3-nitrophenyl)-1,4-dihydropyridine;
(+)-2,6-dimethyl-5-cyano-3-carboethoxy-4-(3-nitrophenyl)-1,4-dihydropyridine;
(−)-2,6-dimethyl-5-carbomethoxy-3-carboethoxy-4-(3-nitrophenyl)-1,4-dihydropyridine.

EXAMPLE 29

A mixture of (+)-2-methylthiomethyl-6-methyl-5-carbomethoxy-3-carboethoxy-4-(3-nitrophenyl)-1,4-dihydropyridine (g 1.9) and methyl iodide (ml 19) is heated at reflux temperature for 48 hours. After filtration, the solution is evaporated to dryness and the residue is dissolved in DMF (ml 20). The stirred solution, cooled at 0°-5° C., is treated with 0.18 g of sodium borohydride, added at small portions. The mixture is then left at room temperature for 30 minutes and diluted with water (100 ml) and extracted with AcOEt. g 1.6 of (+)-2,6-dimethyl-5-carbomethoxy-3-carboethoxy-4-(3-nitrophenyl)-1,4-dihydropyridine, m.p. 158°-159° C., $[\alpha]_D = +16.3°$, $[\alpha]_{546} = +20.5°$ (c=2,1 EtOH) are obtained after the usual work-up and crystallization from Et$_2$O.

EXAMPLE 30

By desulphuration of an enantiomerically pure isothiourea and/or enantiomerically pure isothiouronium salt prepared in accordance with one of procedures of examples 28 and 19, and/or by desulphuration of an enantiomerically pure 2-thioalkyl-1,4-dihydropyridine prepared in accordance with one of the procedures of examples 9 19, starting from one of the isothioureae and/or isothiouronium salts prepared in accordance with procedures of example 19-29, the following enantiomerically pure 1,4-dihydropyridines are prepared:
(+)-2,6-dimethyl-3-carboethoxy-5-carbomethoxy-4-(2,3-dichlorophenyl)-1,4-dihydropyridine, m.p. 139°-141° C.; $[\alpha]_D = +3.9°$, $[\alpha]_{546} = -4.9°$, c=4 CH$_2$Cl$_2$;
2-methyl-3-isopropoxycarbonyl-5-carbomethoxy-4-(2,3-dichlorophenyl)-6-fluoromethyl-1,4-dihydropyridine, enantiomer (+): $[\alpha]_D = +43°$; enantiomer (−): $[\alpha]_D = -42.8°$, c=5 DMF;
(+)-2,6-dimethyl-3-isopropoxycarbonyl-5-carbomethoxy-4-(benzofurazan-4-yl)-1,4-dihydropyridine,
(−)-2,6-dimethyl-3-carboethoxy-5-carbomethoxy-4-(3-nitrophenyl)-1,4-dihydropyridine, m.p. 158°-159° $[\alpha]_D = -15.8°$, c=2.1 EtOH;
2,6-dimethyl-3-carbomethoxy-5-isopropoxycarbonyl-4-(3-nitrophenyl)-1,4-dihydropyridine, m.p. 133°-136° C.; enantiomer (+): $[\alpha]_D = +22°$; enantiomer (−): $[\alpha]_D = -23.5°$; EtOH, c=2.7;
(±)-2,6-dimethyl-3-carboethoxy-5-isopropoxycarbonyl-4-(3-nitrophenyl)-1,4-dihydropyridine, m.p. 139°-141° C.

EXAMPLE 31

At room temperature and under a nitrogen atmosphere, a stirred solution of 13 g of (−)-S-[6-methyl-3-allyloxycarbonyl-5-carbomethoxy-4-(3-nitrophenyl)-1,4-dihydropyridin-2-yl]-methylisothiourea in MeOH (ml 120) is treated with methyl iodide (g 4.3) and 15 ml of a 10% aqueous solution of NaOH for 4 hours.

The mixture is concentrated to a small volume under vacuum, diluted with water and extracted with AcOEt (3×40 ml), to give after the usual work-up g 11.9 of (−)2-methylthiomethyl-6-methyl-3-allyloxycarbonyl-5-carbomethoxy-4-(3-nitrophenyl)-1,4-dihydropyridine.
A stirred solution of this compound in anhydrous 1,2-dimethoxyethane (ml 80) is cooled to 0°-5° C., and treated with g 12.3 of trimethyloxonium tetrafluoroborate to separate at room temperature after about 45 minutes a precipitate of (−)-S-dimethyl-[6-methyl-3-allyloxycarbonyl-5-carbomethoxy-4-(3-nitrophenyl)-1,4-dihydropyridin-2-yl]-methylsulphonium tetrafluoborate (g 12.2) that is filtered and dissolved in DMF (ml 60). To the stirred solution, cooled to 5°-10° C., g 1.3 of sodium borohydride are added in small portions during a 5 minute period. 45 minutes after, the mixture is diluted with water (ml 340) and extracted with AcOEt. The usual work-up gives g 9.7 of: (−)-2,6-dimethyl-3-allyloxycarbonyl-5-carbomethoxy-4-(3-nitrophenyl)-1,4-dihydropyridine.

A solution of 8 g of said compound in dioxane (100 ml) is treated with triphenylphosphine (b 0.15), ammonium formate (g 3.2) and 10% Pd on C (0.25 g) and the mixture is refluxed for 1 hour. After cooling and filtration, the filtrate is concentrated to a small volume, diluted with water, adjusted to pH 8.2/8.5 with N NaOH and extracted with Et$_2$O (3×25 ml) to remove neutral impurities. The basic aqueous phase is acidified with 2N H$_2$SO$_4$ to separate, at a pH 1.2 a crystalline precipitate (g 6.4) of (−)-2,6-dimethyl-3-carbomethoxy-5-carboxy-4-(3-nitrophenyl)-1,4-dihydropyridine, m.p. 215°-217° C.; $[\alpha]_D = -20°$ (c=0.7, acetone).

EXAMPLE 32

Using in the procedure of example 30 the enantiomeric isothiourea, the (+)-2,6-dimethyl-3-carbomethoxy-5-carboxy-4-(3-nitrophenyl)-1,4-dihydropyridine, m.p. 214°-218° C.; $[\alpha]_D = +21°$ (c=0.7) acetone, is obtained, after drying under vacuum. A solution of 0.8 g of this compound in dichloromethane (ml 10) is reacted with PCl$_5$ (g 0.42) at 0° C. for 15 minutes and then at room temperature for one hour. The mixture is then cooled at 30° C. and treated with a solution of 2(N-benzyl,N-methylamino)ethanol (g 2.89) in methylene chloride to give after usual work-up and column purification (SiO$_2$/Et$_2$O/AcOEt 90/10), g 0.3 of (−)-2,6-dimethyl-3-carbomethoxy-5-[2-(N-benzyl-N-methyl)-ethoxy]-carbonyl-4-(3-nitrophenyl)-1,4-dihydropyridine, m.p. 105°-107° C.; $[\alpha]_D = -26°$, c=5, MeOH.

EXAMPLE 33

A solution of S-[6-methyl-3-terbutoxycarbonyl-5-allyloxycarbonyl-4-(2,3-dichlorophenyl)-1,4-dihydropyridin-2-yl)-methyl]-isothiouronium L-mandelate (g 6.7), LiOH (g 1.35) and benzyl chloride (g 1.4) in DMF (ml 40) is stirred, under nitrogen atmosphere and at room temperature, for one hour and is then diluted with a 10% NaH$_2$PO$_4$ aqueous solution (ml 400). After several extractions with Et$_2$O (6×25 ml), the combined organic phases are washed with water, dried and evaporated to dryness. The residue (g 4.97) of 2-benzylthiomethyl-6-methyl-3-tertbutoxycarbonyl-5-allyloxycarbonyl-4-(2,3-dichlorophenyl)-1,4-dihydropyridine is dissolved in 1,2-dimethoxyethane (ml 35) and the solution is cooled to 0°–3° C. and treated with triethyloxonium tetrafluoborate (g 1.7). The precipitate of S-benzyl,ethyl-[6-methyl-3-tertbutoxycarbonyl-5-allyloxycarbonyl-4-(2,3-dichlorophenyl)-1,4-dihydropyridin-2yl]-sulphonium (g 5.04) is dissolved in DMF and treated with g 0.4 of sodium borohydride to give g 3.9 of enantiomerically pure 2,6-dimethyl-3-tertbutoxycarbonyl-5-allyloxycarbonyl-4-(2,3-dichlorophenyl)-1,4-dihydropyridine.

EXAMPLE 34

A solution of g 0.7 of (+)-2-ethylthiomethyl-5-carboxy-4-(2,3-dichlorophenyl)-6-methyl-1,4-dihydropyridine in EtOH (ml 20) and KHCO$_3$ (g 0.21) is added to a stirred Ni-Raney suspension in EtOH (ml 10). After 30 minutes the catalyst is filtered, the filtrate is concentrated to a small volume, diluted with water and acidified to pH 12 with H$_2$SO$_4$ 2N. The crystalline precipitate of (+)-2,6-dimethyl-3-carboethoxy-5-carboxy-4-(2,3-dichlorophenyl)-6-methyl-1,4-dihydropyridine (g 0.47) is collected by filtration and dried under vacuum.

EXAMPLE 35

Using in procedures of examples 23, 31–34 a suitable allylester of 3 and/or 5-carboxy-1,4-dihydropyridine, the following enantiomerically pure carboxylic acids are obtained:

2,6-dimethyl-3-carbomethoxy-5-carboxy-4-(3-nitrophenyl)-1,4-dihydropyridine, 2,6-dimethyl-3-carboethoxy-5-carboxy-4-(2-nitrophenyl)-1,4-dihydropyridine, 2-methyl-6-fluoromethyl-3-carboethoxy-5-carboxy-4-(3-nitrophenyl)-1,4-dihydropyridine, 2-methyl-6-fluoromethyl-3-carboethoxy-5-carboxy-4-(2-nitrophenyl)-1,4-dihydropyridine, 2-methyl-6-formyl-3-carboethoxy-5-carboxy-4-(3-nitrophenyl)-1,4-dihydropyridine, 2,6-dimethyl-3-carbomethoxy-5-carboxy-4-(3-methoxyphenyl)-1,4-dihydropyridine, m.p. 235°–236° C.; enantiomer (+) $[\alpha]_D = +1.5°$; enantiomer (−) $[\alpha]_D = -1.7°$ (c=5 DMF), 2,6-dimethyl-3-carbomethoxy-5-carboxy-4-(3-chlorophenyl)-1,4-dihydropyridine, m.p. 213° C.; enantiomer (+) $[\alpha]_D = +9.5°$, enantiomer (−) $[\alpha]_D = -7.5°$; c=4.7 DMF, (+)-2,6-dimethyl-3-carboxy-5-nitro-4-(3-pyridinyl)-1,4-dihydropyridine, 2,6-dimethyl-3-carbomethoxy-5-carboxy-4-(benzofurazan-4-yl)-1,4-dihydropyridine, 2,6-dimethyl-3-carbomethoxy-5-carboxy-4-(benzodioxan-5yl)-1,4-dihydropyridine, 2,6-dimethyl-3-carbomethoxy-5-carboxy-4-(benzodioxan-6-yl)-1,4-dihydropyridine, (−)-2,6-dimethyl-3-isopropoxycarbonyl-5-carboxy-4-(3-nitrophenyl)-1,4-dihydropyridine, m.p. 194°–195° C.; $[\alpha]_D = -30°$, c=5 DMF, 2,6-dimethyl-3-carboxy-5-cyano-4-(2,3-dichlorophenyl)-1,4-dihydropyridine, 2,6-dimethyl-3-carboxy-5-nitro-4-(2,3-dichlorophenyl)-1,4-dihydropyridine, 2,6-dimethyl-3-terbutoxycarbonyl-5-carboxy-4-(2,3-dichlorophenyl)-1,4-dihydropyridine.

The above compounds, if desired, are then transformed into an activated form of said carboxylic acids (mixed anhydrides, chlorides, imidazolides, hydroxysuccinimide esters) and then reacted with a suitable primary and/or secondary amine and/or with a suitable alcohol to obtain amides and esters of said acids.

EXAMPLE 36

Under inert gas atmosphere, a stirred solution of (+)-[(6-methyl-3-carboethoxy-5-carbomethoxy-4-(3-nitrophenyl)-1,4-dihydropyridin-2-yl)methyl]isothiouronium L-mandelate (g 1) in DMF (ml 7) is added dropwise to a Ni-Raney suspension (g 10) and KHCO$_3$ (g 0.19) in DMF (ml 3). After 1 hour the solution is filtered, added with water (ml 200) and extracted with AcOEt (3×40 ml). The organic phase obtained is washed with water (3×100 ml), anidried on Na$_2$SO$_4$ and the solvent is evaporated under reduced pressure. The crude mixture, recrystallized from Et$_2$O gives mg 430 of (−)-2,6-dimethyl-3-carboethoxy-5-carbomethoxy-4-(3-aminophenyl)-1,4-dihydropyridine, m.p. 176°–179° C., $[\alpha]_D = -6.08°$, $[\alpha]_{578} = -7.00°$, $[\alpha]_{546} = -7.3°$ (c=2.4 CH$_2$Cl$_2$).

EXAMPLE 37

Under inert gas atmosphere and under stirring, a suspension of Ni-Raney (g 4) in acetone (15 ml) is heated to reflux for 2 hours. After cooling at room temperature a solution of (−)-[(6-methyl-3-carboethoxy-5-carbomethoxy-4-(3-nitrophenyl)-1,4-dihydropyridin-2-yl)-methyl]-isothiourea (g 1.5) in acetone (ml 10) is added to it; the mixture is stirred for 2 hours, filtered and evaporated to dryness. The residue is partitioned between AcOEt (ml 30) and aqueous H$_2$SO$_4$ 4N; the organic phase is extracted several times with aqueous H$_2$SO$_4$ 4N (8×5 ml), with water to neutrality and then dried on Na$_2$SO$_4$. By evaporation of the solvent and subsequent crystallization from Et$_2$O, g 0.65 of (+)-2,6-dimethyl-3-carboethoxy-5-carbomethoxy-4-(3-nitrophenyl)-1,4-dihydropyridine $[\alpha]_D = +16.3°$, c=0.7 EtOH are obtained.

The acid extracts are combined and alkalinized to pH 7–8 with aqueous NaOH 2N solution and extracted with AcOEt (3×20 ml). After the usual work-up, g 0.42 of (+)-2,6-dimethyl-3-carboethoxy-5-carbomethoxy-4-(4-aminophenyl)-1,4-dihydropyridine ($[\alpha]_D = +7°$, c=2.3 CH$_2$Cl$_2$) are obtained from the organic phase. Subsequent acetylation gives:

(−)-2,6-dimethyl-3-carboethoxy-5-carbomethoxy-4-(3-acetylaminophenyl)-1,4-dihydropyridine $[\alpha]_D = -1.1°$, c=2.3 DMF.

EXAMPLE 38

Under inert gas atmosphere Ac$_2$O (43 mcl) is added to a stirred solution of (−)-2,6-dimethyl-3-carboethoxy-5-carbomethoxy-4-(3-aminophenyl)-1,4-dihydropyridine (100 mg) in pyridine (ml 1). 90 minutes after dilution with water (ml 50), extraction with AcOEt (3×10 ml) and crystallization from Et$_2$O 70/EtOH 10, give mg 85 of (+)-2,6-dimethyl-3-carboethoxy-5-carbomethoxy-4-(3-acetylaminophenyl)-1,4-dihydropyridine m.p. 197°–199° C. $[\alpha]_D = +0.87°$, $[\alpha]_{578} = +2.00°$, $[\alpha]_{546} = +1.64°$ c=2.2 DMF.

EXAMPLE 39

Under inert gas atmosphere 4N aqueous NaOH (ml 1.93) are added to a stirred solution of (+)-[(6-methyl-3-carboethoxy-5-carbomethoxy-4-(2,3-dichlorophenyl)-1,4-dihydropyridin-2-yl)-methyl]isothiouronium-0,0'-dibenzoyl-D-tartrate (g 0.7) and triethylbenzylammonium chloride (mg 60) in benzene (ml 7). After 5 minutes, the mixture is heated with acetic acid to pH 5, the organic phase is separated, washed with water (3×5 ml), dried on Na$_2$SO$_4$ and the solvent is evaporated under reduced pressure. The crude residue is purified by SiO₂ gel chromatography (30/1; eluent CHCl₃ 90/hexane 20), to give 240 mg of (+)-2-mercaptomethyl-3-carboethoxy-5-carbomethoxy-4-(2,3-dichlorophenyl)-1,4-dihydropyridine, oil [α]$_D$=+17.86°, [α]$_{578}$=19.47°, [α]$_{546}$=+25.12°, c=2.8 CH₂Cl₂.

EXAMPLE 40

Under inert gas atmosphere, a stirred solution of (−)-[(6-methyl-3-carboethoxy-5-carbomethoxy-4-(2,3-dichlorophenyl)-1,4-dihydropyridin-2-yl)-methyl]-isothiouronium-0,0'-dibenzoyl-L-tartrate (g 0.55) and triethylbenzylammonium chloride (mg 46) in benzene (ml 6) is treated with ml 1.5 of aqueous NaOH 4N, after 5' with glacial AcOH up to pH 5. The organic phase is separated, washed with water (3×5 ml), dried on Na₂SO₄. The crude residue is treated in pyridine (6 ml) with mcl 95 of Ac₂O. 40' after, the reaction mixture is diluted with water (ml 100), extracted with Et₂O (3×10 ml); the combined organic phases are washed with water (5×20 ml), dried on Na₂SO₄. After removal of solvent in vacuum the crude residue is crystallized from hexane/Et₂O 50/10, to give mg 240 of (−)-2-acetylthiomethyl-3-carboethoxy-5-carbomethoxy-4-(2,3-dichlorophenyl)-1,4-dihydropyridine, m.p. 155°-157°, [α]$_D$=−16.8°, [α]$_{578}$=−18.44°, [α]$_{546}$=−24.45°, c=2.5 CH₂Cl₂.

EXAMPLE 41

A suspension of 2-methylthiomethyl-6-methyl-4-(3-nitrophenyl)-3-carboethoxy-5-carboallyloxy-1,4-dihydropyridine (g 0.27), palladium on charcoal (10% 6 mg), ammonium formate (mg 71) and triphenylphosphine (mg 3) in anhydrous 1,4-dioxane, is heated at the reflux temperature for 8 hours. The reaction mixture is cooled at room temperature, poured into an aqueous solution of hydrochloric acid (pH=2) and extracted with ethyl acetate (2×20 ml). The combined organic extracts are washed with aqueous sodium carbonate (1N; 3×10 l), the basic washings are collected, acidified to pH 5-6 with diluted aqueous hydrochloric acid. The resulting suspension is extracted with ethyl acetate (2×25 ml) the combined organic extracts are dried on Na₂SO₄ and evaporated under reduced pressure to give mg 160 of 5-carboxy-2-methylthiomethyl-6-methyl-4-(3-nitrophenyl)-3-carboethoxy-1,4-dihydropyridine as an amorphous solid.

NMR (δ, DCDl₃) 10,5 (sb, 1H) 8.3-8.0 (m, 2H) 7.7-7.4 (m, 2H) 7.2 (sb, 1H) 5.2 (s, 1H) 4.3-4.0 (2 q, 4H) 2.4 (s, 3H) 2.0 (s, 3H) 1.25 (t, 3H). M+ 393.

EXAMPLE 42

A sample of (+) tertbutyl,allyl 2,6-dimethyl-4phenyl-1,4-dihydropyridine-3,5-dicarboxylate is treated in dioxane with 10% Pd on C, ammonium formate and triphenylphospine to give (+)-tertbutyl 2,6-dimethyl-4-phenyl-5-carboxy-1,4-dihydropyridine-3-carboxylate.

4-morpholino-ethyl-isonitrile (0.63 ml) is added to a stirred solution of 1,5 g of said acid and 0.86 g of N-hydroxysuccinimide in dry THF (15 ml), cooled at 0° C. The mixture is stirred at room temperature for 30 min., diluted with aqueous N HCl, concentrated in vacuum and extracted with AcOEt to give after the usual work-up a sample of 2,6-dimethyl-4-phenyl-3-tert-butoxycarbonyl-5-carboxy-1,4-dihydropyridine N-hydroxysuccinimido ester. By reaction in DMF of said ester with N-methylpiperazine for an hour at room temperature, dilution with water and usual work-up of the reaction mixture gives N-methyl,N'-(2,6-dimethyl-4-phenyl-3-tertbutoxycarbonyl-1,4-dihydropyridin-5yl)-carbonyl-piperazine.

EXAMPLE 43

A sample of (+) tertbutyl-2,6-dimethyl-4-phenyl-5-carboxy-1,4-dihydropyridine-3-carboxylate is reacted with an ethereal solution of diazomethane to give a sample of (+) tertbutyl,methyl 2,6-dimethyl-4-phenyl-1,4-dihydropyridine-3,5-carboxylate. To a stirred solution of said diester (1.5 g) in chloroform (15 ml), cooled at −12° C., dropwise is added a chloroform (4 ml) solution of trimethylsilyl iodide (0.53 ml) in an hour. The mixture is maintained for a further hour at 0° C., diluted with aqueous Na₂SO₃, acidified with 2N HCl and diluted with water. A white crystalline precipitate of methyl 2,6-dimethyl-4-phenyl-3-carboxy-1,4-dihydropyridine-5-carboxylate (1.14 g) is filtered.

We claim:
1. A process for the preparation of enantiomerically pure 1,4-dihydropyridines of formula I

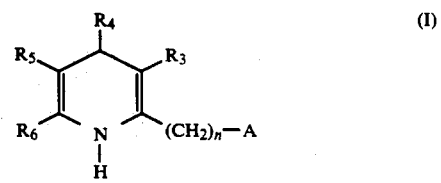

wherein:
A is selected from the group consisting of hydrogen, —SC—(=N—R$_{21}$)—N—R$_{22}$—R$_{23}$, —SH, —S—(C$_2$-C$_{12}$)-aklanoyl, —SR$_2$ and a sulphonium salt of formula —S$^{(+)}$R$_{26}$R$_{27}$y$^{(-)}$;

R$_3$ is a free or esterified carboxy group (—CO$_2$R$_{31}$);

R$_4$ is a member selected from the group consisting of a substituted or unsubstituted phenyl, an unsubstituted α- or β-naphthyl, α, β or γ pyridyl, 2- or 3-furanyl, 2- or 3- thienyl,-1,4-benzodioxan-5-yl, benzofurazan-4-yl, and bezodioxan-6-yl, R$_5$ is selected from the group consisting of a free or esterified carboxy group (—CO$_2$R$_{32}$), —C≡N, —NO$_2$, —CO—NH—R$_{51}$, —P(O)(OR$_{51}$)$_2$ and a CO—R$_{52}$ group;

R$_6$ is selected from the group consisting of a (C$_1$-C$_6$)-alkyl, (C$_1$-C$_4$)-halo-alkyl, —CHO, —C≡N, a carboxyester (—CO$_2$R$_{33}$), an acetal —CH(OR$_{61}$)(OR$_{62}$) and a linear or cyclic thioacetal —CH(SR$_{61}$)(SR$_{62}$);

R$_2$ is selected from the group consisting of a substituted or unsubstituted phenyl, a (CH$_2$)$_n$-Het group wherein Het is 4,5-dihydroimidazol-2-yl, 1,4,5,6-tetrahydropyrimidyn-2-yl, 1-methyl-4,5-dihydroimidazol-2-yl, 1-formyl-1,4,5,6-tetrahydropyrimidyn-2-yl, α-, β- or γ-pyridyl, 2-furyl, a (C$_2$-C$_6$) alkenyl or alkinyl chain, a (C$_1$-C$_6$)alkyl chain unsubstituted or substituted by one or more substituents selected from a free or esterified carboxy group (—CO$_2$R$_{34}$), —C≡N, —O—R$_{24}$, —S—R$_{24}$, —N(R$_{24}$)R$_{25}$, Cl, Br, I, a substituted or unsubstituted phenyl, carbonyl, cis or trans oxyrane, and aziridine groups;

R$_{21}$, R$_{22}$ and R$_{23}$, are independently selected from hydrogen, (C$_1$-C$_4$)-alkyl, phenyl-(C$_1$-C$_4$)-alkyl or (C$_1$-C$_4$)-acyl, or R$_{21}$ and R$_{22}$ taken together with the carbon atom to which they are linked to form a group —(CH$_2$)$_n$— wherein n is an integer 2 to 4;

$R_{24}$ and $R_{25}$ are independently hydrogen, ($C_1$-$C_4$)-alkyl, phenyl($C_1$-$C_4$)-alkyl, cyano-($C_1$-$C_4$)-alkyl, ($C_1$-$C_4$)-alkoxycarbonyl-($C_1$-$C_4$)-alkyl, benzoyl, and ($C_1$-$C_4$-acyl);

$R_{26}$ and $R_{27}$, that can be the same or different, are a ($C_1$-$C_6$)-alkyl or phenyl-($C_1$-$C_6$)-alkyl group;

$R_{31}$, $R_{32}$, $R_{33}$ and $R_{34}$, that may be the same or different, are selected from ($C_1$-$C_4$)-alkyl, ($C_1$-$C_3$)-alkoxy-($C_1$-$C_4$)-alkyl, ($C_2$-$C_6$)-alkenyl or phenyl-($C_2$-$C_6$)-alkenyl, mono- di- or tri-halo-alkyl;

$R_{51}$ is selected from the group consisting of a ($C_1$-$C_4$)-alkyl, ($C_1$-$C_3$)-alkoxy-($C_1$-$C_4$)-alkyl, aryl and aryl-($C_1$-$C_4$)-alkyl;

$R_{52}$ is selected from the group consisting of a ($C_1$-$C_4$)-alkyl and a phenyl;

$R_{61}$ and $R_{62}$ are selected from the group consisting of ($C_1$-$C_4$)-alkyl and phenyl-($C_1$-$C_4$)-alkyl, and each of $OR_{61}$, $OR_{62}$, $SR_{61}$ or $SR_{62}$, taken together with the carbon atom to which they are linked, form respectively a 1,3-dioxolane or a 1,3-dithiolane ring, which may be optionally substituted by ($C_1$-$C_3$)-alkyl or halo-($C_1$-$C_3$)-alkyl;

$y^{(-)}$ is a monovalent anion selected from the group consisting of chlorine, bromine, iodine and $BF_4^{-}(\text{---})$;

n is an integer 1 to 4, comprising:

a) salification of racemic isothioureides of formula II

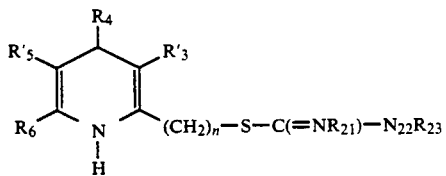

wherein $R_{21}$, $R_{22}$, $R_{23}$, $R_4$, $R_6$ and n are as above defined for formula I while $R_3'$ and $R_5'$ have the same meanings as in formula I except for the free carboxyl, with chiral HB* acids;

b) separation of diastereoisomeric isothiouronium salts of formula $Ia_1$.HB* and $Ia_2$.HB*

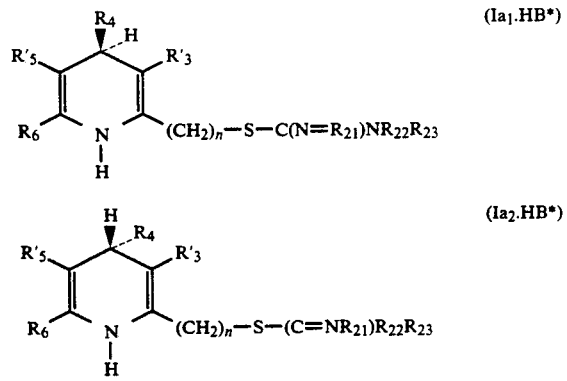

wherein $R_{21}$, $R_{22}$, $R_{23}$, $R_3'$, $R_5'$, $R_4$, $R_6$ and n are as above defined, and their transformation into the corresponding isothioureae or into other isothiouronium salts with achiral acids;

c) optional transformation of compounds $Ia_1$, $Ia_2$ or their salts into other compounds I wherein A is SH, S—($C_1$-$C_{24}$)-acyl, —$SR_2$, or —$S^{(+)}R_{26}R_{27}y^{(-)}$ wherein $R_2$, $R_{26}$ and $R_{27}$ are as defined for formula I; and d) optional transformation of compounds of formula $Ia_1$, into compounds I wherein A is hydrogen, by means of desulfuration under suitable conditions.

2. A process according to claim 1, wherein $R_5$ is a $CO_2R_{31}$ group and one of groups $R_{31}$ or $R_3$ is an allyl residue of formula —$CH_2$—CH=CH—$R_{33}$, wherein $R_{33}$ is hydrogen, $C_1$-$C_3$alkyl or phenyl, comprising, subsequently to the resolution phase, selective hydrolysis of the allyl ester, optionally followed by esterification, hydrolysis of the other carboxyester group and its esterification under suitable conditions and with suitable sequences, so as to convert an isomer into the other by inversion of the $R_3$ and $R_5$ groups.

3. A process according to claim 2, wherein the selective hydrolysis of the allyl ester is carried out under transfer hydrogenolysis conditions, in presence of an hydrogen transfer catalyst, of a phosphine and of an ammonium or alkylammonium salt.

4. A process according to claim 2, wherein one of the carboxyesters is t-butyl or tri-chloroethyl ester.

5. A process according to claim 1 for the preparation of compounds I wherein A is hydrogen comprising desulphuration of compounds I wherein A is a group —$S^{+}(R_{26})R_{27}y^{(-)}$ by means of metal hydrides.

6. A process according to claim 1 for the preparation of compounds I wherein A is hydrogen, comprising desulphuration of compounds I wherein A is SH, —$SR_2$ and S—($C_1$-$C_{24}$)acyl by means of Ni-Raney or Na/Hg amalgams.

7. A process according to claim 5, wherein the group $R_4$ does not include $NO_2$ or alkylthio groups.

8. A process according to claim 5 for the preparation of optical isomers of nitrendipine, nimodipine, nisoldipine, nicardipine, niludipine, felodipine, isradipine, ryodipine, amiodipine, nivaldipine and FR 34235 (nilvadipine).

9. A process for the preparation of optical isomers of 1,4-dihydropyridines of formula I

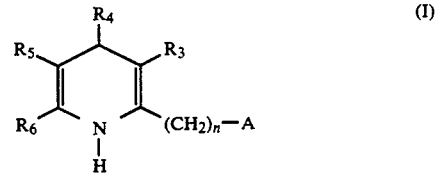

(I)

wherein:

A is hydrogen;

$R_3$ is a free or esterified carboxy group (—$CO_2R_{31}$);

$R_4$ is a member selected from the group consisting of a substituted or unsubstituted phenyl, an unsubstituted α- or β-naphthyl, α, β or γ pyridyl, 2- or 3-furanyl, 2- or 3- thienyl,-1,4-benzodioxan-5-yl, benzofurazan-4-yl, and benzodioxan-6-yl, $R_5$ is selected from the group consisting of a free or esterified carboxy group (—$CO_2R_{32}$), —C≡N, —$NO_2$, —CO—NH—$R_{51}$, —P(O)($OR_{51}$)$_2$ and a CO—$R_{52}$ group;

$R_6$ is selected from the group consisting of a ($C_1$-$C_6$)-alkyl, ($C_1$-$C_4$)-halo-alkyl, —CHO, —C≡N, a carboxyester (—$CO_2R_{33}$), an acetal —CH($OR_{61}$)($OR_{62}$) and a linear or cyclic thioacetal —CH($SR_{61}$)($SR_{62}$);

$R_2$ is selected from the group consisting of a substituted or unsubstituted phenyl, a $(CH_2)_n$-Het group wherein Het is 4,5-dihydroimidazol-2-yl, 1,4,5,6-tetrahydropyrimidyn-2-yl, 1-methyl-4,5-dihydroimidazol-2-yl, 1-formyl-1,4,5,6-tetrahydropyrimidyn-2-yl, α-, β- or γ-pyridyl, 2-furyl, a ($C_2$-$C_6$) alkenyl or alkinyl chain, a ($C_1$-$C_6$)alkyl chain unsubstituted or substituted by one or more substituents selected from a free or esterified carboxy group (—$CO_2R_{34}$), —C≡N, —O—$R_{24}$, —S—$R_{24}$, —N($R_{24}$)$R_{25}$, Cl, Br, I, a substituted or unsubstituted phenyl, carbonyl, cis or trans oxyrane, and aziridine groups;

$R_{21}$, $R_{22}$ and $R_{23}$, are independently selected from hydrogen, ($C_1$-$C_4$)alkyl, phenyl-($C_1$-$C_4$)-alkyl or ($C_1$-$C_4$)-acyl, or $R_{21}$ and $R_{23}$ taken together with the carbon atom to which they are linked to form a group —($CH_2$)$_n$— wherein n is an integer 2 to 4;

$R_{24}$ and $R_{25}$ are independently hydrogen, ($C_1$-$C_4$)-alkyl, phenyl($C_1$-$C_4$)-alkyl, cyano-($C_1$-$C_4$)alkyl, ($C_1$-$C_4$)-alkoxycarbonyl-($C_1$-$C_4$)-alkyl, benzoyl, and ($C_1$-$C_4$)-acyl);

$R_{26}$ and $R_{27}$, that can be the same or different, are a ($C_1$-$C_6$)-alkyl or phenyl-($C_1$-$C_6$)-alkyl group;

$R_{31}$, $R_{32}$, $R_{33}$ and $R_{34}$, that may be the same or different, are selected from ($C_1$-$C_4$)-alkyl, ($C_1$-$C_3$)-alkoxy-($C_1$-$C_4$)-alkyl, ($C_2$-$C_6$)-alkenyl or phenyl-($C_2$-$C_6$)-alkenyl, mono- di- or tri-halo-alkyl;

$R_{51}$ is selected from the group consisting of a ($C_1$-$C_4$)-alkyl, ($C_1$-$C_3$)-alkoxy-($C_1$-$C_4$)-alkyl, aryl and aryl-($C_1$-$C_4$)-alkyl;

$R_{52}$ is selected from the group consisting of a ($C_1$-$C_4$)-alkyl and a phenyl;

$R_{61}$ and $R_{62}$ are selected from the group consisting of ($C_1$-$C_4$)-alkyl and phenyl-($C_1$-$C_4$)-alkyl, and each of $OR_{61}$, $OR_{62}$, $SR_{61}$ or $SR_{62}$, taken together with the carbon atom to which they are linked, form respectively a 1,3-dioxolane or a 1,3-dithiolane ring, which may be optionally substituted by ($C_1$-$C_3$)-alkyl or halo-($C_1$-$C_3$)-alkyl;

$Y^{(-)}$ is a monovalent anion selected from the group consisting of chlorine, bromine, iodine and $BF_4^{-}$(—); and n is an integer 1 to 4, wherein an optical isomer of 1,4-dihydropyridines of formula I, wherein A is S—($C_{21}$-$C_{24}$-acyl); —$SR_2$ or —$S^{(+)}R_{26}R_{27}Y^{(-)}$ and $R_2$, $R_3$, $R_4$, $R_5$, $R_6$, $R_{21}$, $R_{22}$, $R_{23}$, $R_{24}$, $R_{25}$, $R_{26}$, $R_{27}$, $R_{31}$, $R_{32}$, $R_{33}$, $R_{34}$, $R_{51}$, $R_{52}$, $R_{61}$, $R_{62}$, $Y^{(-)}$ and n are as defined above, is desulphurated.

* * * * *